United States Patent
Smith et al.

(12) 
(10) Patent No.: US 6,537,807 B1
(45) Date of Patent: Mar. 25, 2003

(54) HEMATOPOIETIC STEM CELLS

(75) Inventors: Clayton A. Smith, Durham, NC (US); Robert W. Storms, Durham, NC (US); Eli Gilboa, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/205,181

(22) Filed: Dec. 4, 1998

Related U.S. Application Data

(60) Provisional application No. 60/067,305, filed on Dec. 4, 1997.

(51) Int. Cl.[7] ................................................ C12N 5/08
(52) U.S. Cl. .......................... 435/325; 435/2; 435/372
(58) Field of Search .................................. 435/325, 372, 435/2

(56) References Cited

U.S. PATENT DOCUMENTS

| | | |
|---|---|---|
| 5,061,620 A | 10/1991 | Tsukamoto et al. |
| 5,643,741 A | 7/1997 | Tsukamoto et al. |

FOREIGN PATENT DOCUMENTS

| WO | WO 96/39489 | 12/1996 |
|---|---|---|

OTHER PUBLICATIONS

Cincuttini et al, A Novel Population of Natural Killer Progenitor Cells Isolated from Human Umbilical Cord Blood, The Journal of Immunology 151(1):29–37 (1993).

Bárcena et al, "Phenotypic and Functional Analysis of T–Cell Precursors in the Human Fetal Liver and Thymus: CD7 Expression in the Early Stages of T–and Myeloid–Cell Development", Blood 82(11):3401–3414 (1993).

Mossalayi et al, "Human Marrow CD7+CD2–CD34–Cells Are Committed to T Cell Lineage: Possible Filiation From Earlier 34+CD7+Precursor", J. Cell Biochem. Supp 16C:79 (1992), Abstract No. M232.

Nakauchi, "Hematopoietic stem cells: Are they CD34–positive or CD34–negative?", Nature Medicine 4(9):1009–1010 (1998).

Bhatia et al, "A newly discovered class of human hematopoietic cells with SCID–repopulating activity", Nature Medicine 4(9):1038–1045 (1998).

Bonnet et al, "Development of conditions for the ex vivo culture of a novel CD34 population of primitive human hematopoietic repopulating cells", Blood 90(10) Suppl 1 (Part 1 of 2), Nov. 15, 1997, Abstract No. 703.

Hansteen et al, "CD34+, but not CD34+ cells with the human hoescht 33342 'side popu . . . possess primitive pluripotent progenitor activity", Blood 90(10) Suppl 1 (Part 1 of 2), Nov. 15, 1997, Abstract No. 704.

Punzel et al, "Human bone marrow (BM) CD34+/HLA–DR– cells expressing CD2 and/or contain primitive myeloid LTCIC with similar growth characteristics as lineage depleted progenitors", Blood 90(10) Suppl 1 (Part 1 of 2), Nov. 15, 1997, Abstract No. 705.

Storms et al, "Novel CD7+ hematopoietic cells isolated from human umbilical cord blood", Blood 90(10) Suppl 1 (Part 1 of 2), Nov. 15, 1997, Abstract No. 2130.

Storm et al, "Characterization of Hematopoietic Cells Isolated From Human Umbilical Cord Blood Using Hoechst 33342", Blood 88 (10 sup 1):157 (1996).

Goodell, M.A., et al. Isolation and Functional Properties of Murine Hematopoietic Stem Cells that are Replicating *In Vivo*, J. Exp. Med. vol. 183, 1996, pp. 1797–1806.

*Primary Examiner*—David Saunders
(74) *Attorney, Agent, or Firm*—Alston & Bird LLP

(57) ABSTRACT

The present invention relates to hematopoietic stem cells and to methods of treating diseases and disorders, including genetic diseases and disorders and infectious diseases, using same. The invention additionally relates to methods of identifying agents that promote growth, engraftment or differentiation of stem cells.

9 Claims, 23 Drawing Sheets

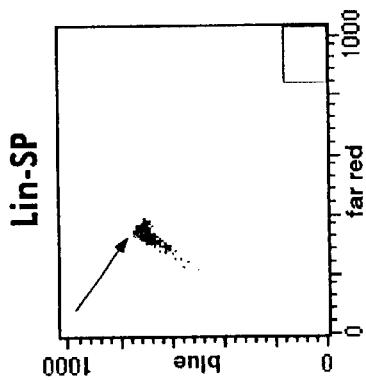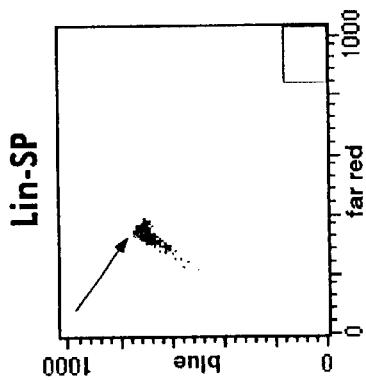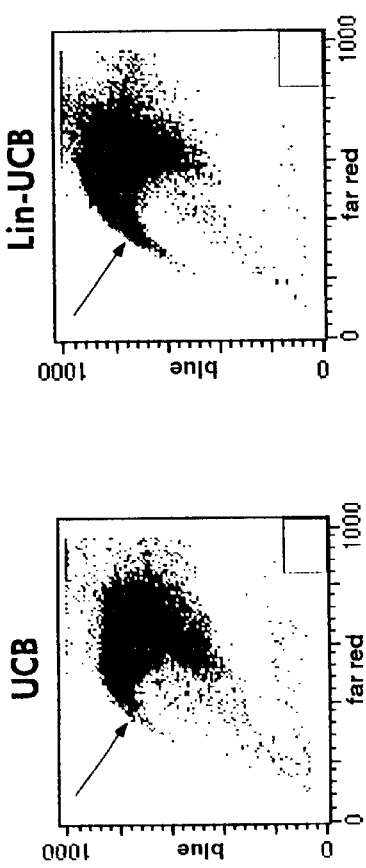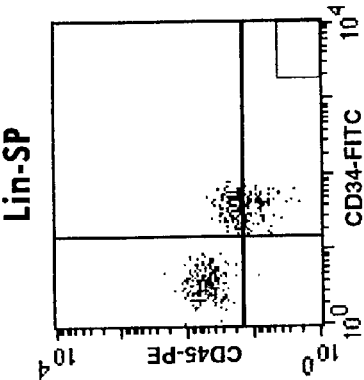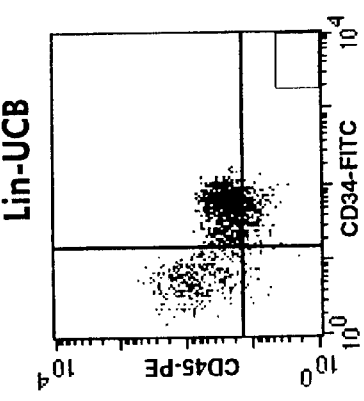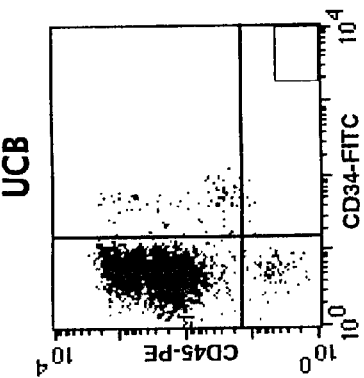

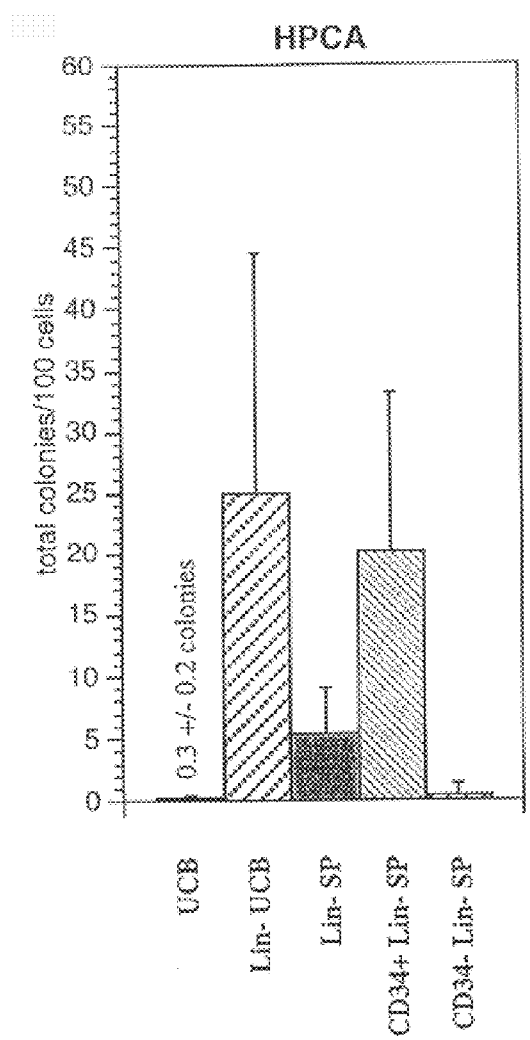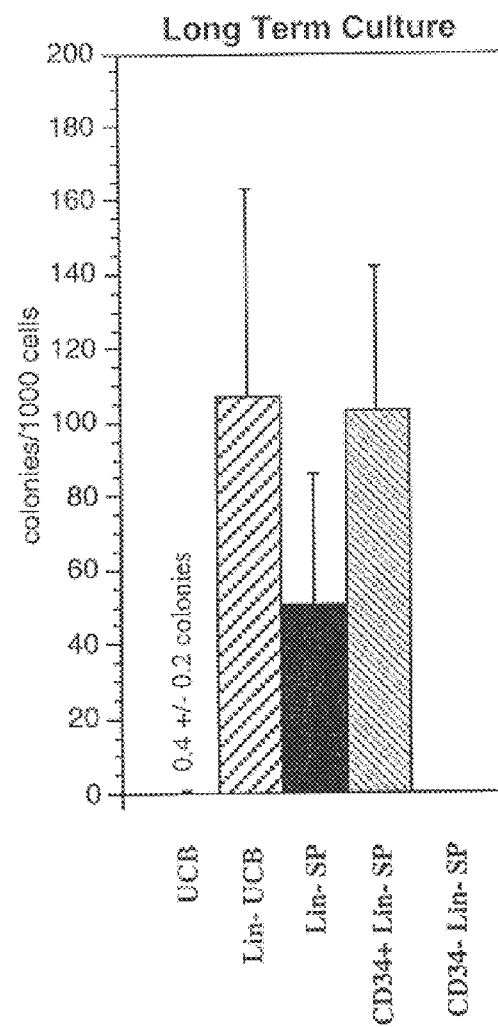

C.

D.

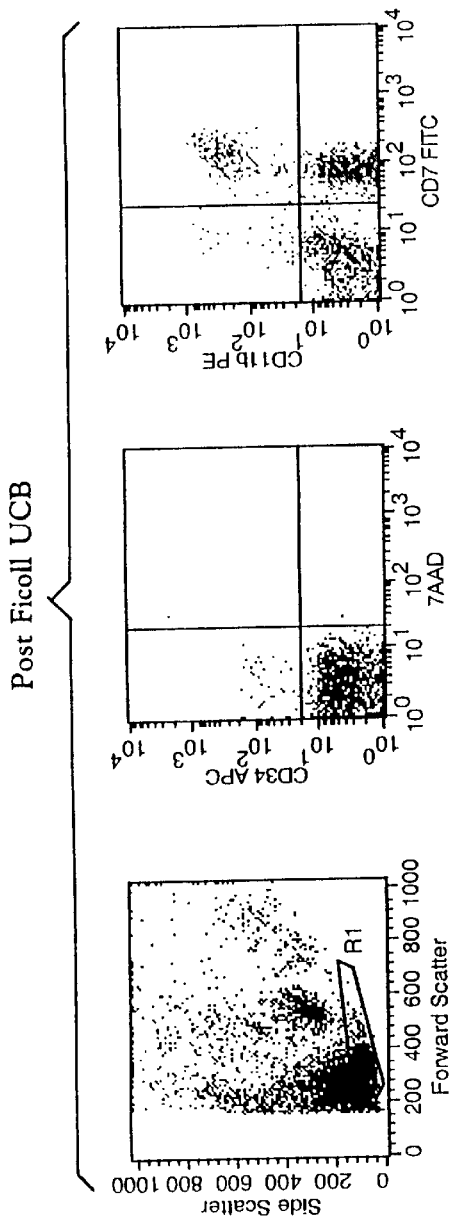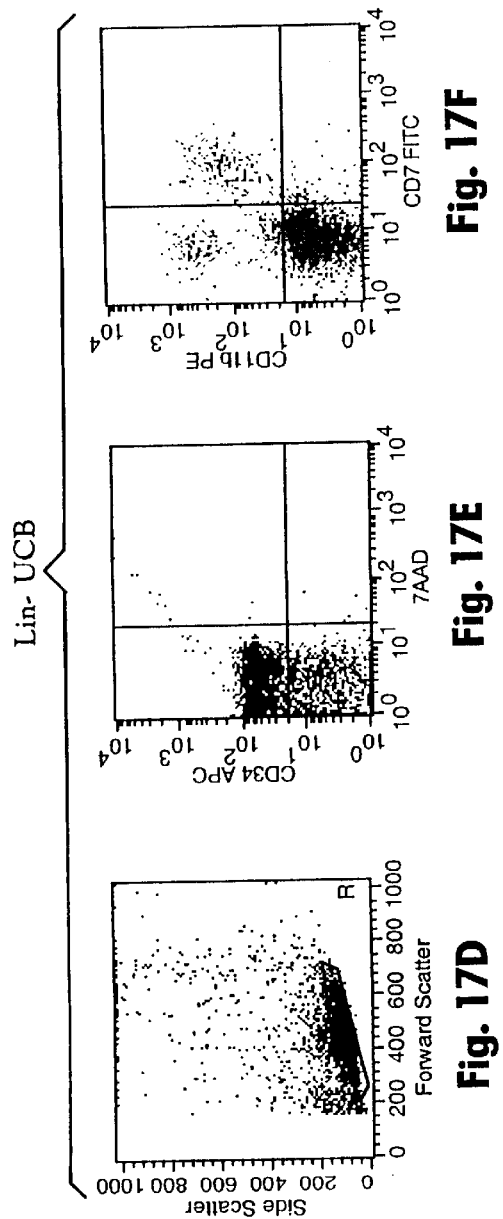

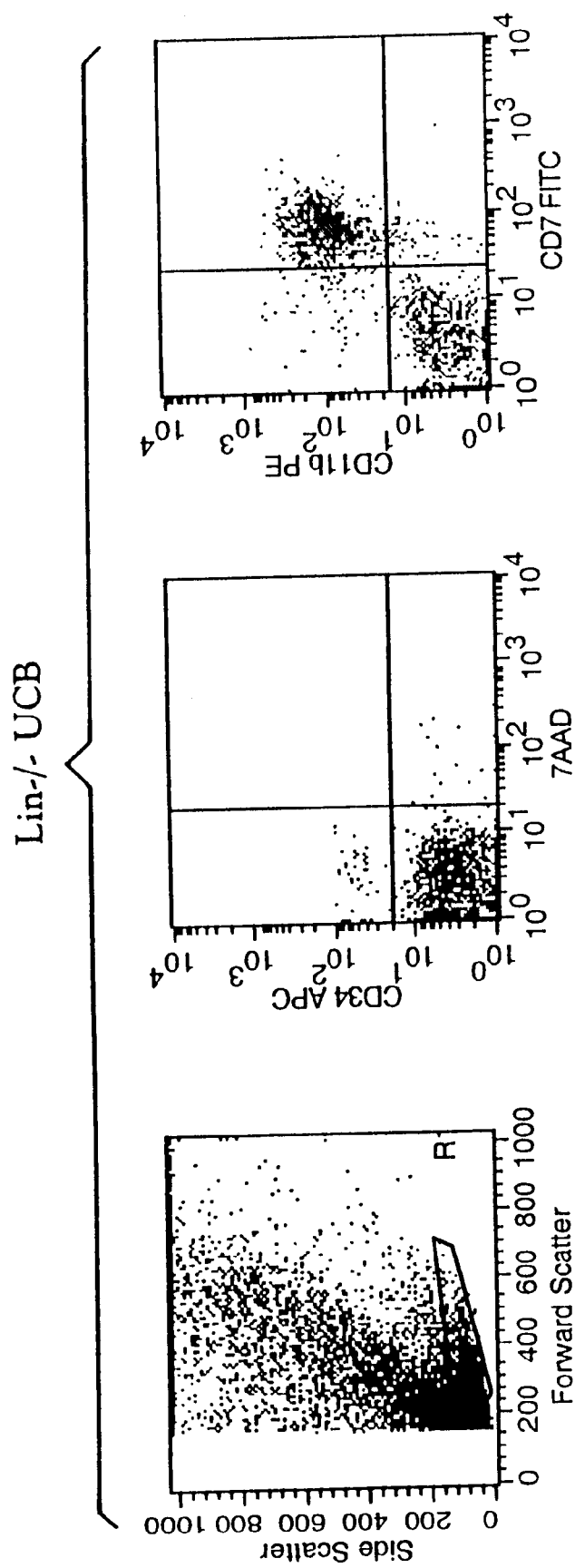

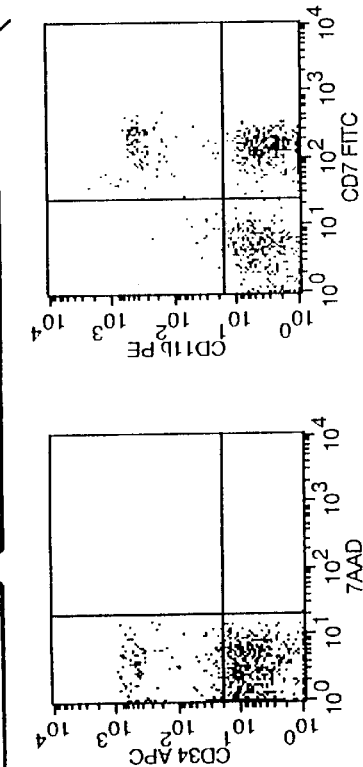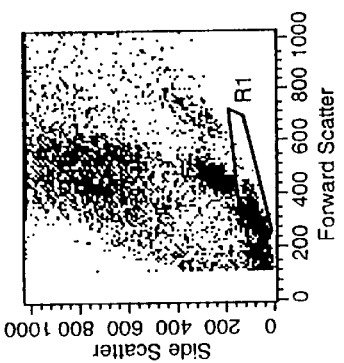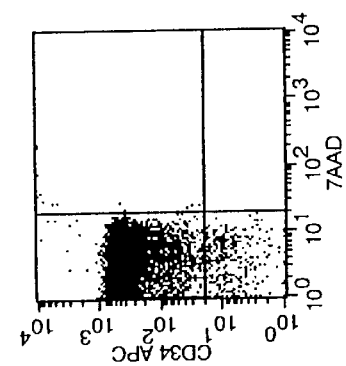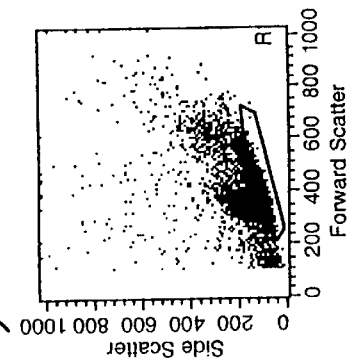

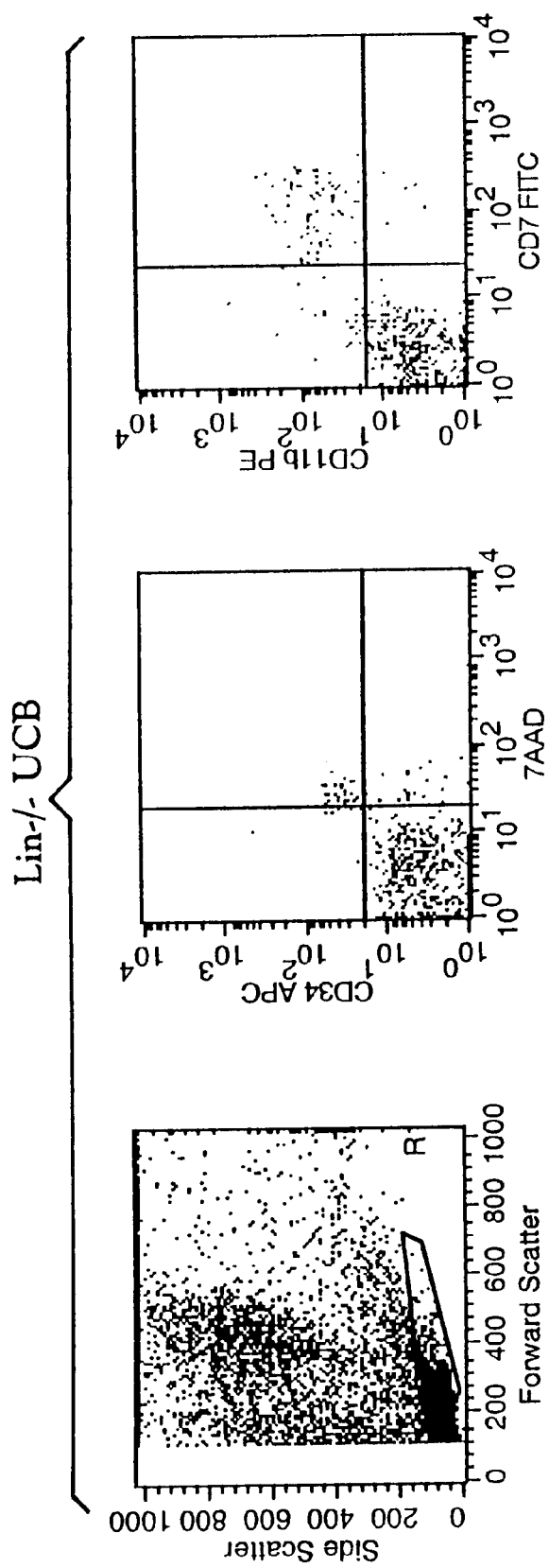

HEMATOPOIETIC STEM CELLS

This application claims priority from Provisional Application No. 60/067,305, filed Dec. 4, 1997, the entire contents of which is incorporated herein by reference.

The present invention was made with funds from the National Institutes of Health, Grant No. R37-AI-28771-08. The Government has certain rights in this invention.

TECHNICAL FIELD

The present invention relates to hematopoietic stem cells and to methods of treating diseases and disorders, including genetic diseases and disorders and infectious diseases, using same. The invention additionally relates to methods of identifying agents that promote growth, engraftment or differentiation of stem cells.

BACKGROUND

The ability to isolate and manipulate hematopoietic stem cells (HSC) for the purposes of gene therapy and transplantation has drawn intensified interest in recent years (Emerson, Blood 87:3082 (1996); Karlsson, Blood 78:2481 (1991)). Functionally, the most primitive hematopoietic stem cells have extensive potential for self renewal and can give rise to all blood cell lineages. Currently, however, the phenotype of the most primitive human hematopoietic stem cells remains unclear. Primitive human hematopoietic progenitors with extensive potential for self renewal and multilineage development have been characterized by numerous groups using both in vitro assays and chimeric animal models. These studies suggest that the most primitive human HSC express the CD34 surface marker (CD34$^+$), lack obvious lineage commitment markers (Lin$^-$) and express low to undetectable levels of other cell surface markers including CD38, CD71 CD45RA, and Thy-1 (Terstaypen et al, Blood 77:1218 (1991); Landsdorp et al, J. Exp. Med. 178:787 (1993); Cicuttini et al, Growth Factors 10:127 (1994); De Bruyn et al, Stem Cells 13:281 (1995); Di Giusto et al, Blood 84:421 (1994); Hao et al, Blood 86:374 (1995); Huang et al, Blood 83:1515 (1994); Muench et al, Blood 83:3170 (1994); Rusten et al, Blood 84:1473 (1994)). Despite this evidence, to date there have been no human transplant studies to formally determine the phenotype of the most primitive human hematopoietic stem cells.

Recently, three studies using long term murine bone marrow transplant models have indicated that there are populations of primitive HSC that express low to undetectable amounts of CD34 (CD34$^{lo-}$ cells) and that are capable of durably generating lymphoid and myeloid lineages following their transplantation. Osawa et al (Science 273:242 (1996)) demonstrated that a single Lin$^-$c-kit$^+$Ly6A/Sca-1$^+$CD34$^{lo/-}$ cell could result in long term hematopoietic reconstitution in recipient mice. Jones et al (Blood 88:487 (1996)) identified a population of small Lin$^-$CD34$^{lo/-}$AA4.1$^-$ cells that expressed high levels of aldehyde dehydrogenase that were capable of durably generating lymphoid and myeloid lineages following engraftment. Morel et al (Blood 88:629a (1996)) demonstrated that Lin$^-$thy-1$^{lo}$Ly6A/Sca-1$^+$CD34$^{lo/-}$ cells contain high proportions of long-term repopulating HSCs.

The present invention is based, at least in part, on the finding that human CD34$^-$ HSC exist and that these cells, designed CD7$^+$CD34$^-$Lin$^-$ cells, possess properties consistent with primitive pluripotent cells.

SUMMARY OF THE INVENTION

The present invention relates to hematopoietic stem cells, designated CD7$^+$CD34$^-$Lin$^-$ cells. The invention further relates to methods of treating diseases and disorders using such cells. Examples of diseases that can be treated with the cells of the invention include both genetic and infectious diseases. The invention also relates to methods of identifying agents that can be used to promote growth and engraftment of stem cells, as well as the differentiation of such cells.

Objects and advantages of the present invention will be clear from the description that follows.

BRIEF DESCRIPTION OF THE DRAWINGS

FIG. 1D for murine bone marrow).

FIGS. 3A–3F. Purification of hematopoietic cells in the Lin$^-$SP. Typical Hoechst emission profiles of UCB, Lin$^-$UCB and Lin$^-$SP cells are represented in FIGS. 3A, 3B and 3C, respectively. Typical CD34 and CD45 expression for UCB, Lin$^-$UCB and Lin$^-$SP cells are represented in FIGS. 3D, 3E and 3F. These data were acquired by 4 color FACS® analyses.

FIGS. 7A and 7B), CD45RA (FIGS. 7C and 7D), CD71 (FIGS. 7E and 7F) and HLA-DR (FIGS. 7G and 7H) in Lin⁻UCB (FIGS. 7A, 7C, 7E and 7G) with that of the Lin⁻SP (FIGS. 7B, 7D, 7F and 7H). In these analyses, the Lin⁻SP was defined as the dimmest 0.5% of the Hoechst-stained cells. These are represented relative to the expression of CD34. The level of CD34 expression is depicted on the abscissa regardless of the fluorochrome used.

FIGS. 8A–B. Growth of Lin⁻SP cells under myelo-erythroid conditions. UCB wore fractionated by lineage depletion and by FACS® sorting. Hematopoietic progenitors from UCB, Lin⁻UCB, Lin⁻SP, CD34⁺Lin⁻SP and CD34⁺Lin⁻SP fractions were enumerated by HPCA (FIG. 8A) and by long-term culture (FIG. 8B) on MS-5 stroma.

The data from CD34⁺UCB SP cells are derived from a single LTC culture well from each of 2 umbilical cords.

All of the growth indicated for the CD34⁻UCB SP cells was derived from a single LTC well (of 8 culture wells initiated from 3 umbilical cords).

FIGS. 10A–10D. Analysis of Lin⁻UCB and Lin⁻Lin⁻ UCB preparations.

Figure 11B:
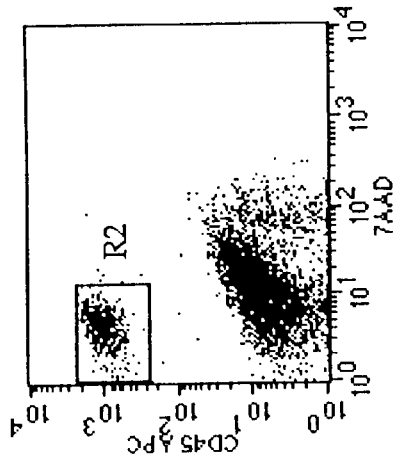
Figure 11E:
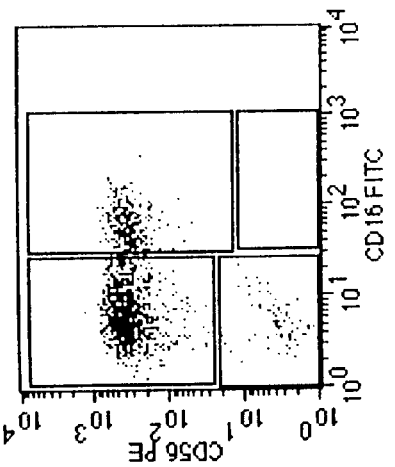
Figure 11A:
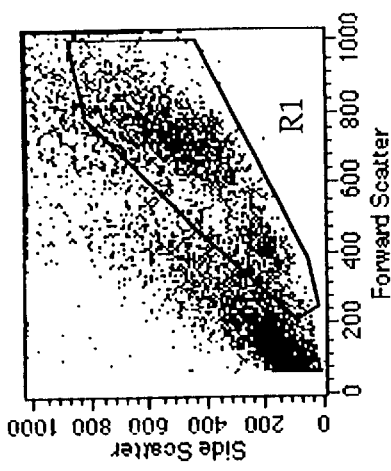
Figure 11D:
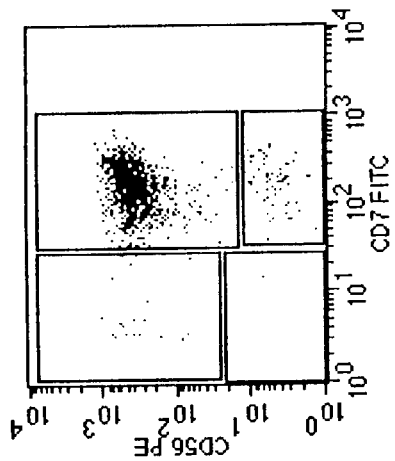
Figure 11C:
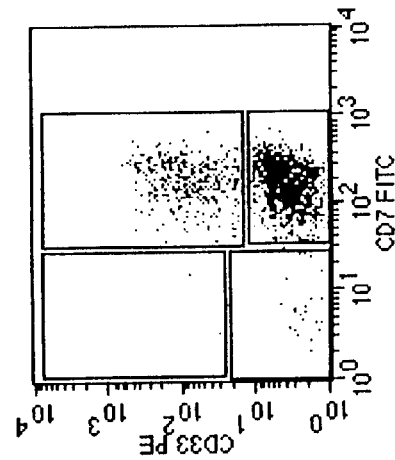
Figure 11H:
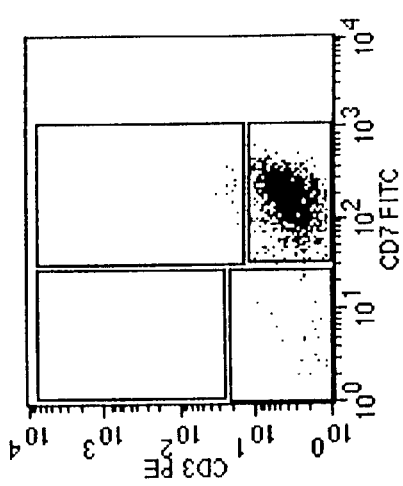
Figure 11G:
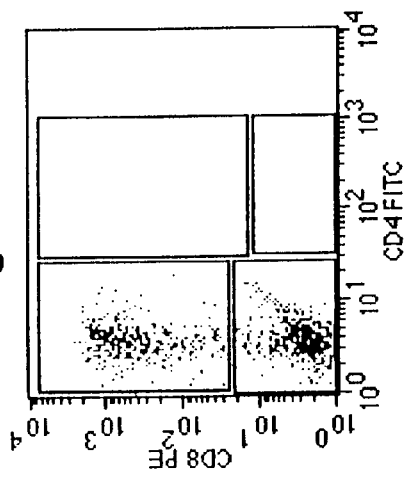
Figure 11F:
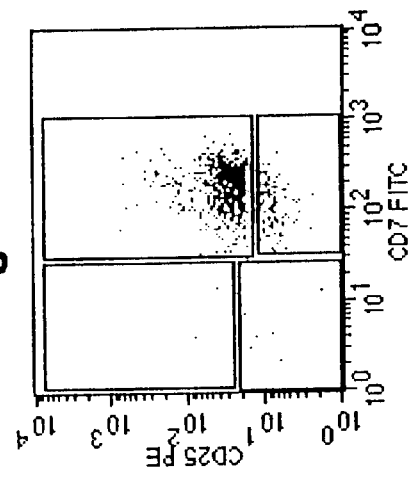
Figure 11J:
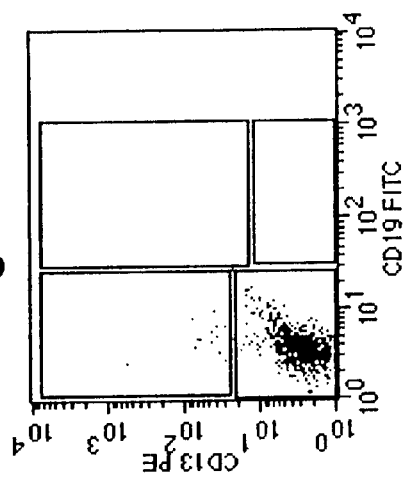
Figure 11I:
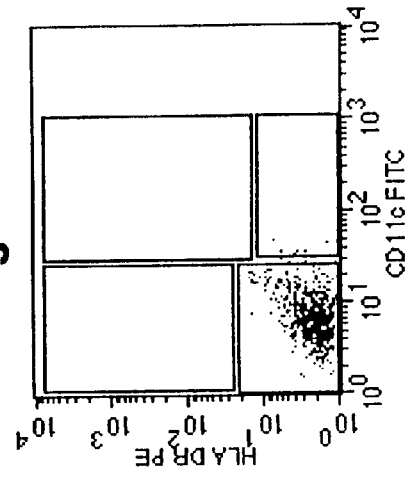

FIGS. 11A–11J. CD34⁻CD7⁺Lin⁻/⁻ cells generate progeny with NK cell markers. CD34⁻CF7⁺Lin⁻/⁻ cells were cultured for 14 weeks on AFT024 (Moore et al, Blood 89:4337 (1997)) supplemented with KL, FLt-3L, C-CSF, TPO, IL-3, IL-7, IL11, and IL-5. Live human cells were defined based on scatter properties (R1 in FIG. 11A) and expression of CD45 coupled with low 7-AAD staining (R2 in FIG. 11B). These cells were then stained for markers of myeloid cells (FIG. 11C), NK cells (FIGS. 11D–F), T-cells (FIGS. 11G–H), DCs (FIG. 11I) and B-cells (FIG. 11J).

Figure 12A:
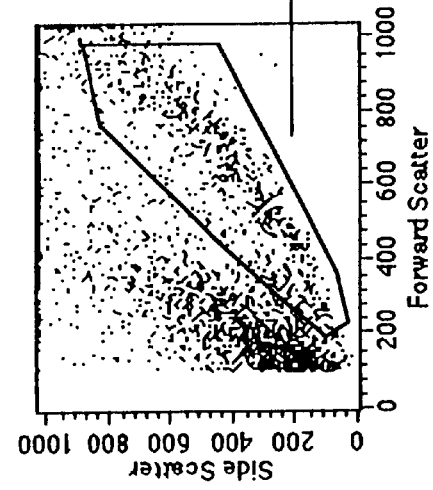
Figure 12B:
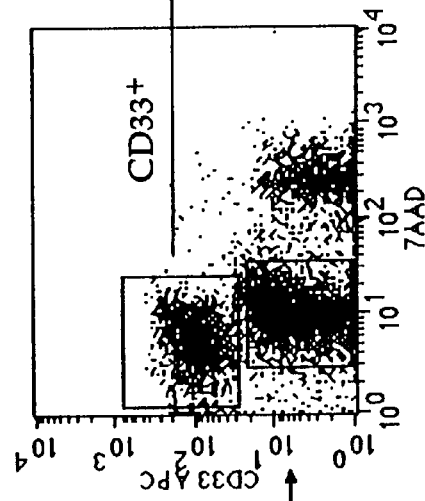
Figure 12C:
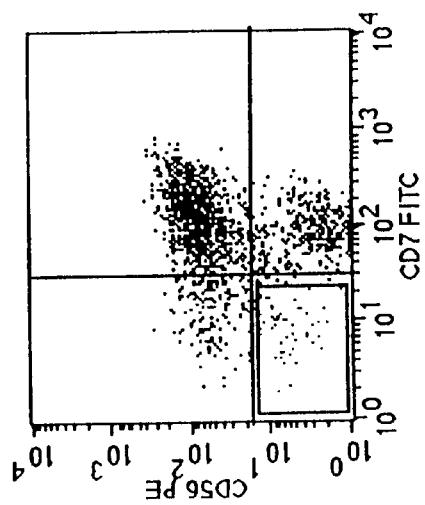

FIGS. 12A–12C. CD34⁻CF7⁻/⁻Lin⁻/⁻ cells generate cells with a myeloid immunophenotype. CD34⁻CF7⁺Lin⁻/⁻ cells were cultured for 28 days on AFT024 stroina supplemented with KL, FL, TPO, G-CSF, IL-7, IL-3, IL-11, and IL-15. The entire culture was harvested and CD33⁺ cells were identified in the population of live human cells defined based on scatter properties (FIG. 12A) and low 7-AAD staining (FIG. 12B). The CD33+ cells were then analyzed for the co-expression of CD56 and CD7 (FIG. 12C). Putative mature CD33+ CD7–CD56– myeloid cells are depicted in red in FIG. 12C.

Figure 13A:
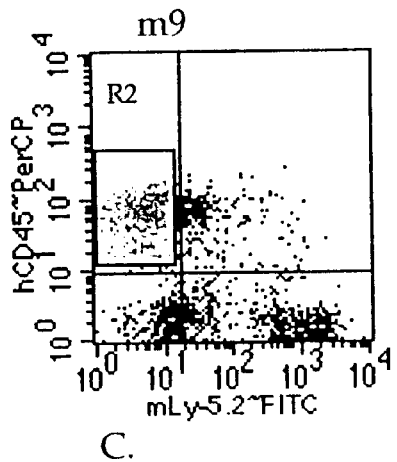
Figure 13B:
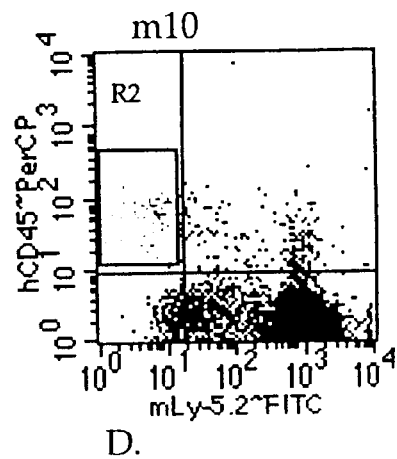
Figure 13C:
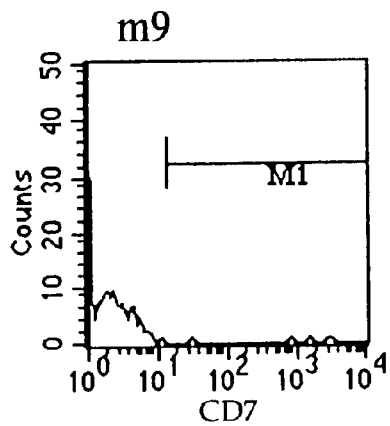
Figure 13D:
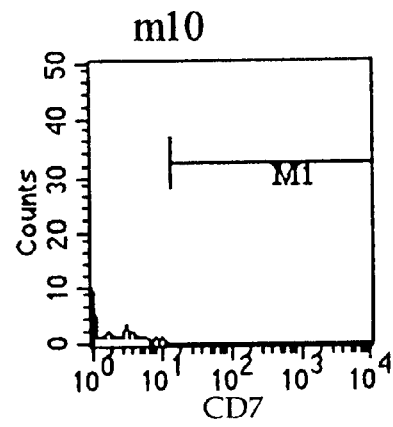
Figure 14A:
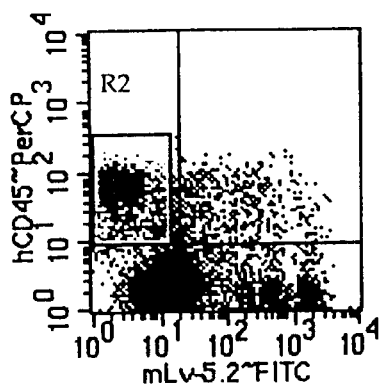
Figure 14B:
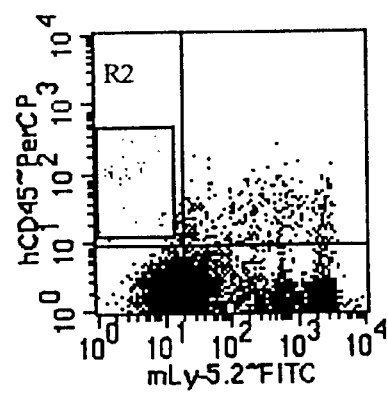
Figure 14C:
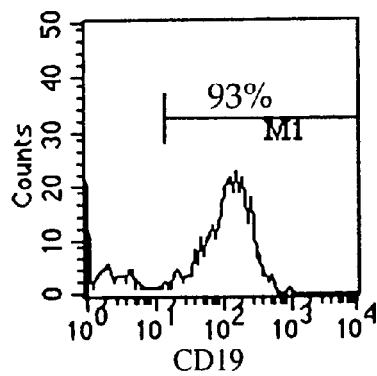
Figure 14D:
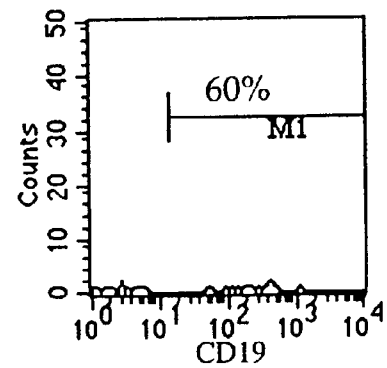

FIGS. 13A–13D. CD34⁻CD7⁺Lin⁻ cells can engraft SCID/NOD mice. SCID/NOD mice were sublethally irradiated and inoculated with ≦4000 CD34⁻CD7⁺Lin⁻/⁻ cells. Mice were sacrificed at 8 weeks and analyzed for the presence of human cells based on anti-CD45 staining (FIG. 13A and 13B). Cells were stained with anti-Ly-2 to exclude murine cells which could have non-specifically stained with anti-CD45 (upper right quadrants in FIGS. 13A and 13B). CD45⁺Ly-2⁻ cells (in green in FIGS. 13A and 13B) were then analyzed for the expression of CD7 (FIGS. 13C and 13D). Data is presented for two mice (m9 and m10) using cells recovered from the thymus.

FIGS. 14A–D. CD34⁻CD7⁺Lin⁻/⁻ cells can generate CD19⁺ cells in SCID/NOD mice. SCID/NOD mice engrafted with control unfractionated UCB (FIG. 14A) and CD34⁻CD7⁺Lin⁻/⁻ cells (FIG. 14B) were analyzed for expression of the B-cell marker CD19 (controls-FIG. 14C, CD34⁻CD7⁺Lin⁻/⁻ cells-FIG. 14D). Data is from one mouse using cell recovered from the spleen.

Figure 15:
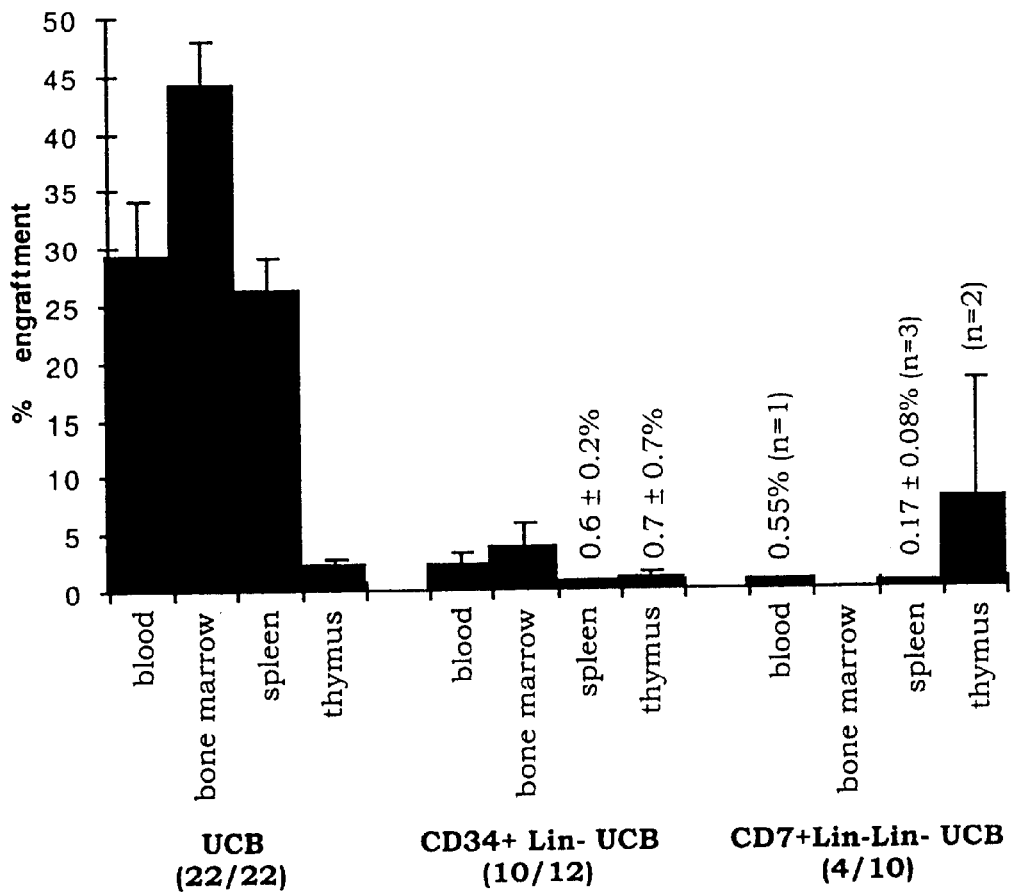

FIG. 15. Summary of SCID/NOD experiments data presented is the mean and standard deviation of 22 mice engrafted with unfractionated $10^7$ UCB cells, 12 mice transplanted with approximately 5×15 CD34⁺Lin⁻UCB and 10 mice transplanted with <4×103 CD34⁻CD7⁺Lin⁻/⁻ cells. The numbers in parentheses below the graft summarize the rate of engraftment for each group. Engraftment levels were determined at 7–8 weeks following transplantation using the criteria described above with reference to FIGS. 13 and 14.

Figure 16A:
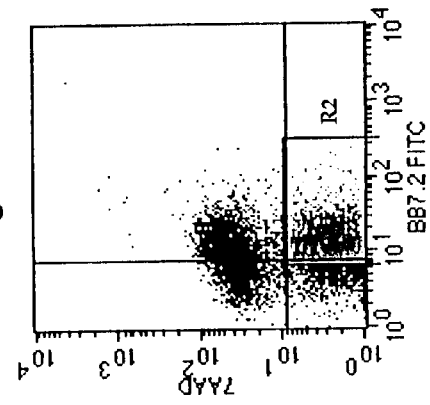
Figure 16B:
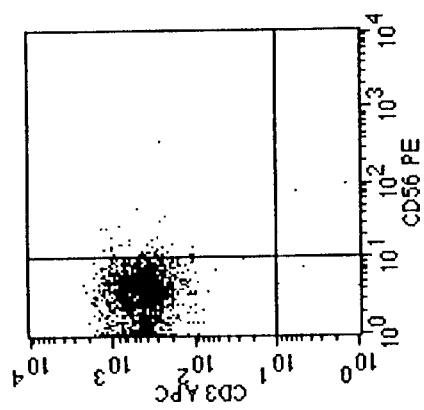
Figure 16C:
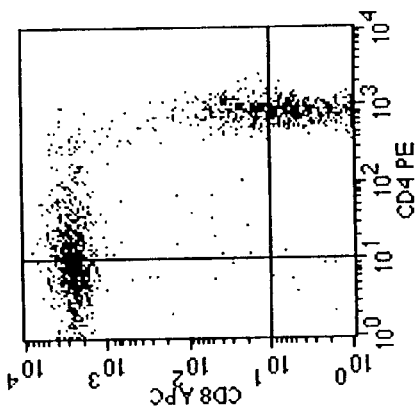
Figure 16D:
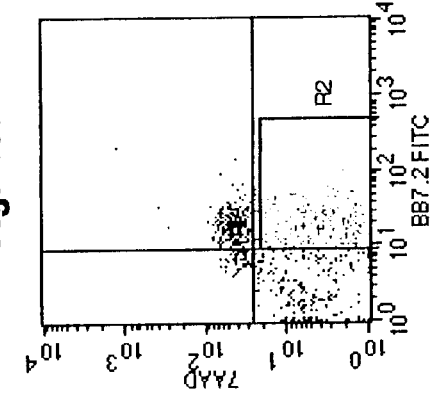
Figure 16E:
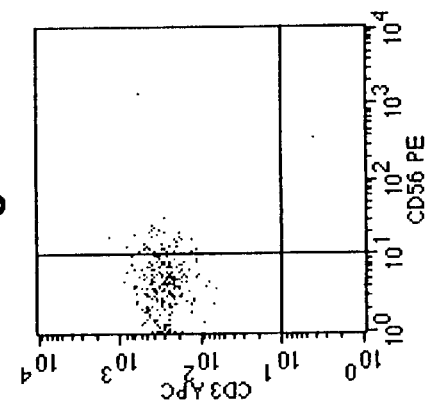
Figure 16F:
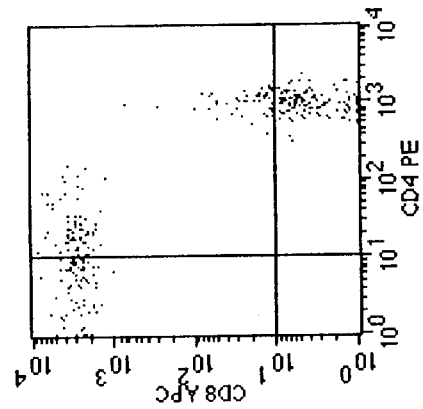

FIGS. 16A–16F. Engraftment of CD34⁻CD7⁺Lin⁻/⁻ cells in SCID/hu thy mice. SCID/hu thy mice established with HLA-AT-thymus grafts Galy et al, Blood 85:2770 (1995) were inoculated with 1200 CD34⁻CD7⁺HLA-A2Lin⁻/⁻ cells. Nine weeks later, thymii were harvested and gated on live (7-AAD–) cells expressing HLA-A2 (detected using the anti-HLA-A2 antibody BB7-FITC) (FITC⁺ cells in FIGS. 16A and 16D). Live HLA-A2+ cells were then analyzed for expression of CD3 and CD56 (FIGS. 16B and 16E) as well as CD4 and CD8 (FIGS. 16C and 16F). Cursors were set based on an isotypic control where <1% of events were positive. The total cell yield from mouse 36-18 (FIGS. 16A–C) was $3.8×10^6$ cells and from mouse 36-19 (FIGS. 16D–F) was $6.8×10^6$ cells.

FIGS. 17A–17I. Two sequential depletions: Mononuclear cells from UCB were first enriched for Lin– cells via StemSep separation. The Lin–UCB cells were then further purified using a cocktail for the Lin–/–UCB.

FIGS. 18A–18I. One single depletion: Mononuclear cells from UCB were enriched for Lin– cells via StemSep separation or for Lin–/–UCB cells using the StemSep cocktail in conjugation with the cocktail for the Lin–/–UCB.

DETAILED DESCRIPTION OF THE INVENTION

The present invention relates to hematopoietic stem cells and methods of isolating same. These cells, designated CD7⁺CD34⁻Lin⁻ stem cells, are defined by their expression of CD7, and lack of expression of CD34. CD7⁺CD34⁻Lin⁻ cells have the properties of primative pluripotent cells. Such cells are, advantageously, human cells.

Included within the invention are cell populations that are greater than about 80% CD7⁺CD34⁻Lin⁻ cells, preferably, greater than about 90% (or 95%), as determined, for example, by standard flow cytometric techniques. Homogenous CD7⁺CD34⁻Lin⁻ cell populations are more preferred. While the isolation of CD7⁺CD34⁻Lin⁻ cells from umbilical cord blood is specifically exemplified herein, the isolation of such cells from other sources including bone marrow, peripheral blood and fetal liver, is also contemplated. CD7⁺ CD34⁻Lin⁻ cells can be isolated from such sources using a variety of techniques, including those provided in the Examples, that follow. For example, a three step isolation procedure can be used. In a first step, mature mononuclear cells, for example, which express any of 9 different surface antigens associated with specific lineage commitment, can be eliminated using, for example, a commercially available kit from StemCell Technologies. The resulting preparation, designated Lin⁻, is essentially devoid of cells expressing any of the following surface antigens: glycophorin A (glyA), CD3, CD2, CD56, CD24, CD19, CD66b, CD14 and CD16. In a second step, a subset of Lin⁻ cells can be isolated by flow cytometry after staining with, for example, Hoechst 33342 dye. The sorted cells represent approximately 1% of the preparation of Lin⁻ cells and are referred to as the Lin⁻SP. This preparation consists of 2 mutually exclusive populations of cells: one of which is $CD7^+CD34^-$, the other being $CD7^+CD34^+$. In a third step, $CD34^+$ cells can be removed from the Lin⁻SP fraction using, for example, flow cytometry, to yield $CD7^+CD34^-Lin^-$ cells.

An alternative isolation procedure involves the use of a single negative depletion step. In accordance with is procedure, cells expressing CD34 and Lin lineage markers are eliminated in a single step using appropriate antibodies (ie those present in the above-referenced StemCell Technologies kit and CD34 specific antibodies). Alternatively, $CD7^+$ cells can first be positively selected, for example, using FACS or immunoabsorbants, followed by depletion of that subpopulation of CD34+ and Lin+ cells, as described above.

Regardless of the isolation procedure used, the resulting $CD7^+CD34^-Lin^-$ cells have properties of primitive hematopoietic stem cells. First, they lack lineage commitment markers, including cell surface markers for immature and mature lymphocytes, erythrocytes or myeloid cells. More specifically, they have no detectable expression of surface markers of myeloid cells (CD33), B-lymphocytes (CD19, HLA-DR), T-lymphocytes (CD3, CD4, CD8), NK cells (CD16, CD56), or erythroid cells (CD71), detectable using fluorescence-conjugated antibodies (see Example 4). The $CD7^+CD34^-Lin^-$ cells also do not have detectable expression of the early lymphoid markers CD10, CD1a, CD2 or CD5. Advantageously, the $CD7^+CD34^-Lin^-$ cells of the invention do not have detectable expression of any of the following antigens: CD34, CD71, CD38, CD33, CD14, CCD13, CD56, CD16, CD2, CD5, CD19, CD4, CD8, CD3, CD2, CD25, CD10, HLA-DR, CD41, glyA, CD130 or CD124. (The cells of the invention can have detectable expression of CD45RA and CD11b.) Second, the $CD7^+CD34^-Lin^-$ cells stain with Hoechst 33342 dye in a manner identical to cells capable of sustaining long term hematopoiesis in mice (Goodell et al, J. Exp. Med. 183:1797 (1996)). Third, the $CD7^+CD34^-Lin^-$ cells are in $G_0$, a cell cycle state that is believed to be a property of primative hematopoietic cells (Spangrude et al, Proc. Natl. Acad. Sci. USA 87:7433 (1990)). Fourth, the immunophenotype of $CD7^+CD34^-Lin^-$ cells is similar to that of multipotent leukemias as described by Kurtzberg et al (J. Exp. Med. 162:1561 (1985); Blood 73:381 (1989)). Specifically, the $CD7^+CD34^-Lin^-$ cells are $CD71^-$, Thy-1⁻ and HLA-DR⁻, indicating they are not committed to erythroid (CD71), T-cell (Thy-1) or B-cell (HLA-DR) lineages (see Example 5). Fifth, $CD7^+CD34^-Lin^-$ cells fail to proliferate in either short term or long term in vitro culture assays that readily support the growth of committed myeloid, erythroid and T-lymphoid progenitors (see Example 6). $CD7^+CD34^-Lin^-$ cells do, however, persist in culture for many months and a system that supports their growth has been defined and is described in Example 8.

The $CD7^+CD34^-Lin^-$ cells of the invention have application in a variety of therapies and diagnostic regimens. As the cells are primative hematopoietic stem cells, they are suitable for both transplantation and gene therapy purposes. For example, isolation of $CD7^+CD34^-Lin^-$ cells from bone marrow or peripheral blood of patients with cancer can provide for the separation of stem cells from cancer cells. In patients undergoing autologous transplantation, such separation can be used to reduce the chance that cancer cells are returned to the patient. Purified autologous $CD7^+CD34^-Lin^-$ cells can be ex vivo expanded to hasten neutrophil, erythroid and platelet engraftment after autologous transplantation. Ex vivo expansion can be effected by growth in defined cytokines, on stromal layers and/or in bioreactors (Emerson et al, Blood 87:3082 (1996)). In addition, the incidence of graft failure can be reduced. This is beneficial for cancer patients undergoing autologous transplantation, for patients suffering from auto-immune disorders, and for patients undergoing gene therapy.

Gene therapy approaches involving the present cells involve, in one embodiment, isolation of autologous $CD7^+CD34^-Lin^-$ cells, exposure of the isolated cells to a gene delivery vector and re-infusion of the modified cells into the patient (Smith, J. Hematother. 1:155 (1992)). This approach can involve ex vivo culture or the use of vectors capable of transferring genes into non-dividing cells, thereby rendering ex vivo culture unnecessary. Gene therapy can be useful in treating, for example, congenital diseases, such as sickle cell anemia, in which case the mutant β-globin gene is replaced or supplemented with either the wild type globin gene or an anti-sickling globin gene. In the treatment of cancer, drug resistance genes can be introduced into $CD7^+CD34^-Lin^-$ cells to confer resistance to cytotoxic drugs. This can reduce the incidence and severity of myelosupporession. For the treatment of infectious diseases, including HIV, anti-viral genes can be introduced into $CD7^+CD34^-Lin^-$ cells so that they are rendered resistant to the virus (Gilboa and Smith, Trends in Genetics 10:139 (1994)).

Isolation of $CD7^+CD34^-Lin^-$ cells results in the elimination of T-cells that cause GvHD. This elimination can be expected to reduce the incidence and severity of GvHD in recipients of allogeneic transplants.

Purified allogenic $CD7^+CD34^-Lin^-$ cells can be ex vivo expanded to hasten neutrophil, erythroid and platelet engraftment after allogeneic transplantation. In addition, the incidence of graft failure can be reduced. This is likely to be particularly important for recipients of umbilical cord blood transplants where small cell doses limit the success of transplantation.

Successful engraftment with $CD7^+CD34^-Lin^-$ cells can also be expected to induce tolerance. Such would clearly enhance solid organ transplantation.

It will be appreciated that cells of the present invention can be used as sources of new genes (eg for cytokines and cytokine receptors), including genes important in growth and development.

In addition to their application in treatment and diagnosis strategies, the $CD7^+CD34^-Lin^-$ cells of the invention can be used in screening protocols to identify agents that can be used, for example, to promote differentiation or growth and/or engraftment of hematopoietic cells. In one such protocol, $CD7^+CD34^-Lin^-$ cells are contacted with a test compound suspected of inducing differentiation and the ability of the test compound to effect differentiation determined (using, for example, microscopic and flow cytometric examination). In another screening protocol, $CD7^+CD34^-Lin^-$ cells are contacted with a test compound suspected of inducing proliferation and/or engraftment and the ability of the test compound to effect proliferation and/or engraftment determined using in vitro long term colony assays or in vivo immunodeficient mice models (eg SCID NOD mice). (See Peault et al, Leukemia 7:s98–101 (1993)).

The invention also relates to kits that can be used to prepare the CD7$^+$CD34$^-$Lin$^-$ cells of the invention. The kits can comprise antibodies that can be used to effect direct isolation of the cells. In a preferred embodiment, the kit includes at least antibodies specific for the following antigens: CD4, CD5, CD13, CD33, CD34, CD38 and CD25 disposed within one or more container means. These antibodies can be used in conjunction with those present in the StemCell Technologies kit to achieve, for example, about 80% purification or higher. Advantageously, the kit also includes antibodies specific for HLA-DR and CD7 1. Any or all of antibodies specific for CD14, CD13, CD56, CD16, CD2, CD19, CD8, CD3, CD10, glyA, CD130 and CD124 can also be included, disposed within at least one container means. The kit can also include, disposed within a container means, anti-CD7 antibodies.

The antibodies of the kits are disposed within a container means and the kit can further include ancillary reagents (eg buffers and the like) suitable for carrying out the isolation protocols.

Certain aspects of the invention are described in greater detail in the non-limiting Examples that follow.

EXAMPLES

The following experimental details are referenced in certain of the specific Examples that follow.

Antibody reagents. Directly-conjugated fluorescent antibodies were employed for all analyses of cell surface antigens. Those used included antibodies directed against CD2 (Leu5; FITC), CD3 (Leu4; PerCP), CD5 (Leu1; PE), CD7 (Leu9; FITC), CD10 (CALLA; FITC), CD11b (Leu5; PE), CD19 (Leu12; FITC), CD33 (LeuM9; PE), CD34 (HPCA2; FITC and PE), CD38 (Leu17; PE), CD56 (Leu19; PE) and HLA-DR (FITC) from Becton Dickinson Immunocytometry Systems (BDIS; San Jose, Calif.). Anti-CD7 (3A1; PE) and anti-CD45 (KC56; PE) were purchased from Coulter Corporation (Hialeah, Fla.); anti-CD16 (3G8; PE) as well as the pooled anti-CD34 antibodies (QBEnd10, Immu-133, Immu-134; PE) from Immunotech, Inc. (Westbrook, Me.); anti-CD3 (BB11; FITC) and CD38 (B-A6; FITC) from BioSource International (Camarillo, Calif.); anti-CD45RA (F8-11-13; PE) from Southern Biotechnology Associates, Inc. (Birmingham, Ala.); and anti-CDw90 (5E10; PE) from PharMingen, Inc. (San Diego, Calif.).

Isolation of murine bone marrow. Marrow was extracted from femurs of C57B1/6 mice (Charles Rivers Laboratories, Raleigh, N.C.) and a single cell suspension was prepared in Dulbecco's modified MEM (DMEM) by passage of the marrow through an 18 gauge syringe needle. Debris was removed by filtering the cell suspension through a narrow gauge wire mesh. The cells were then washed and resuspended at $10^6$ cells/ml in DMEM supplemented with 2% fetal calf serum (FCS) and 10 mM HEPES, pH 7.4. Murine cells were labeled with 5 mg/ml Hoechst 33342 (Sigma Chemical, St. Louis, Mo.) for 90 minutes at 37° C. In some experiments, verapamil (American Regent Laboratories, Shirley, N.Y.) was added at a final concentration of 50 mM during the staining with Hoechst.

Cell isolation and lineage depletion. Human umbilical cord blood (UCB), intended for disposal, was collected into sterile bottles containing anticoagulant citrate buffer by the staff of the Labor and Delivery ward at Duke University Medical Center. The UCB used in these studies were processed within 18 hours of being harvested. The UCB was diluted 1:2 with Dulbecco's phosphate buffered saline (PBS) and red blood cells were agglutinated at room temperature using Hespan (DuPont Pharma, Wilmington, Del.) brought to a final concentration of 1%. Non-agglutinated white blood cells were harvested and residual red cells were hemolysed at 37° C. in 0.17 M NH$_4$Cl containing 10 mM Tris-HCl, pH 7.2 and 200 mM EDTA. For depletions of lineage-committed cells, the white cell fractions of UCB were brought to $6-8 \times 10^7$ cells/ml in PBS/2% FCS and were depleted using the CD34$^+$ StemSep enrichment cocktail (StemCell Technologies Inc., Vancouver, BC) according to kit instructions. The recovered cells were termed Lin$^-$ cells. The Lin$^-$UCB cells were washed in DMEM with 10% FCS and were held on ice in DMEM/10% FCS until used for fluorescence-activated cell sorting. When held overnight, the cells were kept on ice in a 4° C. refrigerated room.

Cell staining and fluorescence-activated cell sorting using Hoechst. Undepleted or Lin$^-$UCB cells were resuspended at $10^6$ cells/ml in DMEM/2% FCS/10 mM HEPES, pH 7.4 (staining media) and preincubated at 37° C. for 30 min. The cells were then labeled with 2.5 mg/ml Hoechst in the same media for 90 min. When used, verapamil was included at 50 mM. After staining, the cells were washed 3 times with ice cold staining media, resuspended, and maintained on ice until analysis and sorting. For 2 color analyses of Hoechst-stained cells, the cells were then resuspended in staining media with 1 mg/ml propidium iodide (PI) (Sigma Chemicals). For antibody staining to permit 4 color analyses, the cells were resuspended in staining media (100 ml) and antibodies were added directly to the cell suspensions. The cells were incubated on ice for 20–30 min. and then washed 3 additional times in ice cold staining media and resuspended in staining media containing 1 mg/ml PI. The cells were then analyzed or sorted on a FACStar Plus cell sorter equipped with dual Coherent I-90 lasers. The Hoechst was excited at 351 nm and emissions were detected using 45ODF20 (blue) and LP675 (far red) filters (Omega Optical Inc., Brattleboro, Vt.). A 610 nm short pass dichroic mirror was used to separate these emission wavelengths (Omega Optical Inc.). Emissions from the Hoechst dye were acquired in linear scales. Dead and dying cells were excluded on the basis of their high emission in the far red wavelength due to their uptake of PI.

For analyses of cell surface antigens on cells previously sorted based on Hoechst staining, cells were pelleted and resuspended in 100 ml PBS with 2% FCS and held on ice. Fluorescence-conjugated antibodies were added directly to the cell suspensions. Following incubations for 20–30 minutes, the cells were washed 3 times in PBS/2% FCS. Where necessary, the cells were fixed in 1% formaldehyde in PBS/2% FCS. In all surface marker analyses, no differences were noted between 4 color analyses with cells stained simultaneously with Hoechst and with antibodies and those analyses performed on FACS® sorted SP cells that were subsequently stained with antibodies.

For intracellular staining, FACS® isolated cells were stained using the Fix and Perm cell permeabilization kit according to the manufacturer's instructions (Caltag Laboratories, South San Francisco, Calif.) and an anti-CD3-PerCP conjugate (Leu4; BDIS).

Wright Giemsa staining. In preparation for differential staining, cells in PBS were pelleted for 3 minutes at 1000 rpm directly onto coated slides using a Cytospin3 centrifuge (Shandon, Inc., Pittsburgh, Pa.). The cells were stained with Wright Giemsa stain in an automated cell stainer in the Pediatric Bone Marrow Transplant laboratory at Duke University Medical Center.

Hematopoieticprogenitor colony (HPC) assays and long term culture (LTC) assays. To assess Lin$^-$CD34$^+$SP and Lin⁻CD34⁻SP cells in short and long term cultures, multiple sequential sorts were employed to ensure the utmost purity of Lin⁻CD34⁺ and Lin⁻CD34⁻SP cells. First, SP cells were initially sorted as 1–2% of the Hoechst-stained Lin⁻UCB. This included only those cells at the dimmest tip of the SP profile (see FIG. 3B for a representative profile). The isolated Lin⁻SP cells were then resorted based on their expression of CD34 and CD38. To achieve the optimal discrimination between the CD34⁻ and CD34⁺ subpopulations, cells were stained with a phycoerythrin conjugate of anti-CD34, since this is more sensitive than the FITC conjugate. Thus, the selection of CD38$^{lo}$/⁻ cells was based on a FITC-conjugated reagent. This reagent is considerably more dim than the PE-conjugated anti-CD38 typically used to define CD38 expression on primitive HSC (Hao et al, Blood 86:3745 (1995); Thoma et al, Blood 83:2103 (1994)). Because of this, only the brightest CD38⁺ cells were excluded from these culture assays. With this strategy, an average of 7% of the CD34⁻SP cells and 28% of the CD34⁺SP cells were excluded based on their expression of CD38. For the purposes of these isolations, CD38⁻ was defined as cells having a signal intensity equivalent to, or less than, the FITC isotype control. In some experiments, CD34⁺ and CD34⁻SP cells were isolated directly from unfractionated UCB which had been stained simultaneously with Hoechst and anti-CD34-phycoerythrin.

Hematopoietic progenitor colony assays were performed by plating 100–200 cells in MethoCult H4431 (StemCell Technologies, Inc.). The cells were incubated in a humidified chamber at 37° C. with 5% CO$_2$. Hematopoietic colonies (>100 cells) were then scored at 14 to 18 days after initiating the cultures. Long term cultures were maintained on either irradiated allogeneic bone marrow stroma or stromal layers of murine MS-5 cells (provided by Dr. Tadashi Sudo of the Kirin Pharmaceutical Research Laboratory, Gunma, Japan; (Issaad et al, Blood 81:2916 (1993)). The MS-5 stromal layers were established by seeding the center wells of 24-well plates (Corning Costar Corp., Cambridge, Mass.) with 6–7×10⁴ MS-5 cells/well in 0.5 ml DMEM supplemented with 10% FCS. These cells were cultured at 37° C. in a humidified incubator until the cultures approached approximately 80% confluence. The monolayers were then irradiated with 30 Gy g-irradiation from a cesium source. After irradiation, the culture media from the monolayers was replaced entirely with Myelocult H5100 (StemCell Technologies) and the cells were maintained at 33° C. in a humidified chamber with 5% CO$_2$. Long term cultures were typically initiated with 500–2000 hematopoietic progenitor cells/well on the irradiated MS-5 cells. At 7–10 day intervals half the media from each well was removed so that the media could be replenished. Adherent and non-adherent cells were harvested after weeks and plated into HPC assays as described above.

Example 1

Identification of a Hoechst 33342 Side Population in Human Umbilical Cord Blood

Figure 1A:
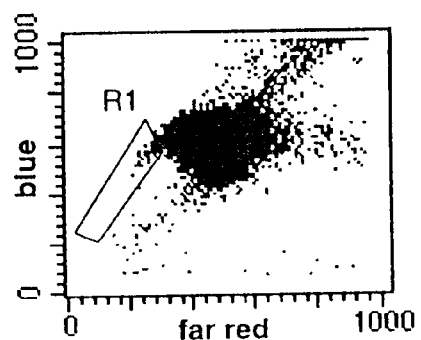
FIGS. 1A–1D. Hoechst staining and emission profiles. The staining and emission profile of human UCB labeled with 2.5 μg/ml Hoechst (FIG. 1A) was compared with that of murine bone marrow labeled with 5 μg/ml Hoechst (FIG. 1B). The side population (SP) cells are indicated by the gates drawn (R1 in UCB; R2 in murine bone marrow) and are absent in similar cell populations labeled with Hoechst in the presence of 50 μM verapamil (FIG. 1C for UCB.
Figure 1B:
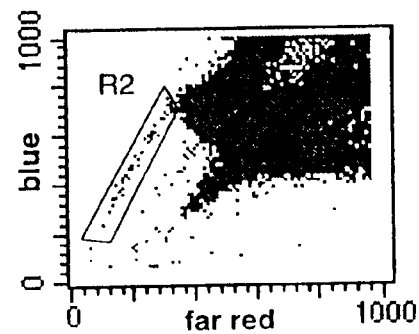
Figure 1C:
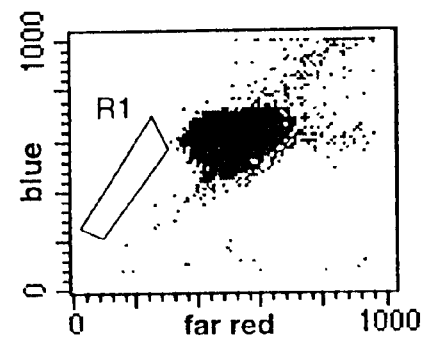
Figure 1D:
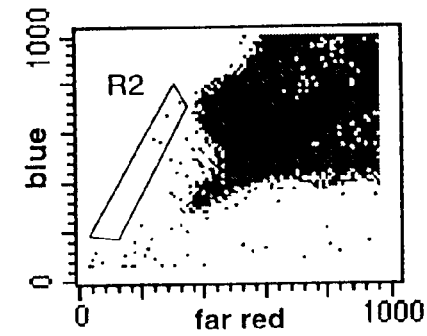

To identify SP cells in human UCB, initial studies were conducted to establish an optimal Hoechst concentration and staining duration. Several conditions produced a similar pattern; however, incubation of UCB with 2.5 mg/ml of Hoechst for 90 minutes consistently identified a population of cells with a staining and fluorescence emission pattern like that of murine bone marrow SP (FIGS. 1A and 1B). Goodell et al (J. Exp. Med. 183:1797 (1996)) have previously shown that the Hoechst SP profile in murine bone marrow was blocked by the addition of verapamil (FIG. 1D), indicating that the dim staining of SP cells was at least partially due to the efflux of Hoechst by a multidrug resistance (MDR) like protein. The UCB SP subpopulation was also verapamil-sensitive (FIG. 1C) and represented 0.35 0.15% of the total white cell content of UCB. However, this population included cells that comprise a "shoulder" of the staining and emission profile that could not be easily distinguished from the main population of cells in the absence of verapamil treatment. Consequently, the UCB SP was defined as the dimmest tip of the verapamil sensitive UCB cells, which typically represented 0.1–0.2% of the total white cell content (R1 in FIGS. 1A and 1C). This was comparable to the SP of murine bone marrow, which typically represented approximately 0.1% of the total white cells (R2 in. FIGS. 1B and 1D) (Goodell et al, J. Exp. Med. 183:1797 (1996)).

Example 2

Characterization of the SP in Unfractionated UCB

Figure 2A:
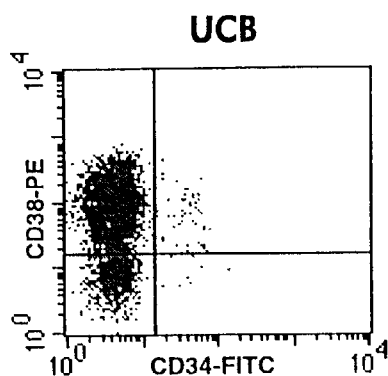
FIGS. 2A–2J. Expression of lineage commitment markers in the UCB SP. Four color FACS® analyses were used to compare the expression of CD34 in unfractionated UCB (FIGS. 2A, 2C, 2E, 2G and 2I) with that found within the UCB SP (FIGS. 2B, 2D, 2F, 2H and 2J). The SP in these analyses was defined as the dimmest 0.1% of the Hoechst-stained cells. This expression is represented relative to that of CD38 (FIGS. 2A and 2B), CD45 (FIGS. 2C and 2D), CD33 (FIGS. 2E and 2F), CD16 and CD56 (FIGS. 2G and 2H) and CD4 (FIGS. 2I and 2J).
Figure 2B:
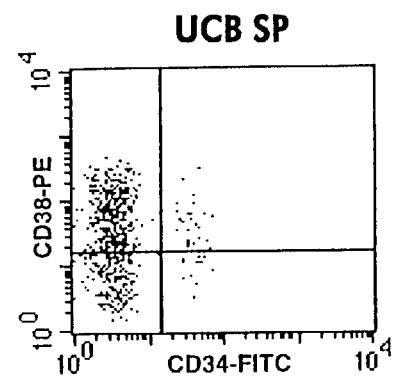
Figure 2C:
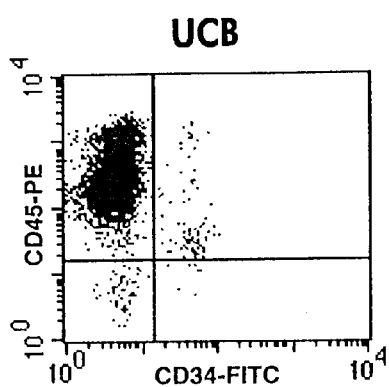
Figure 2D:
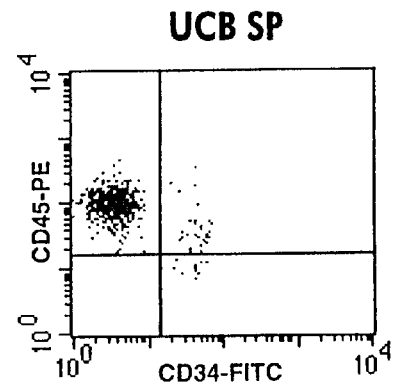
Figure 2E:
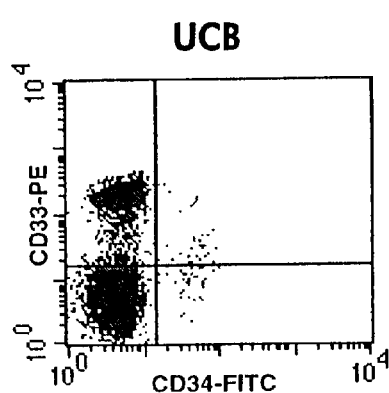
Figure 2F:
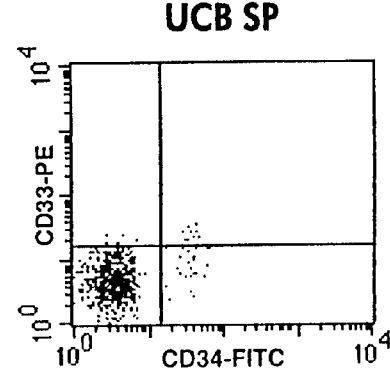
Figure 2G:
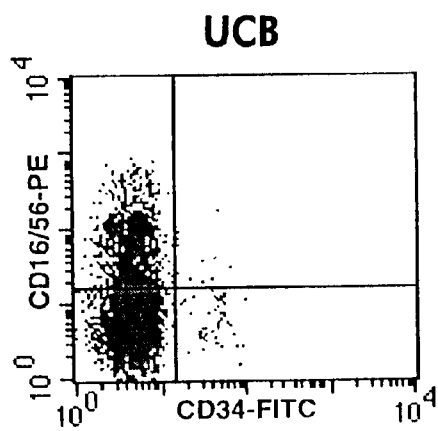
Figure 2H:
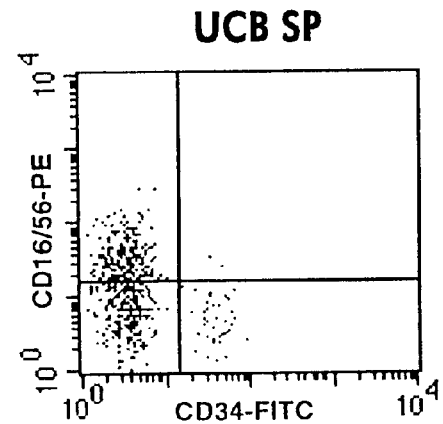
Figure 2I:
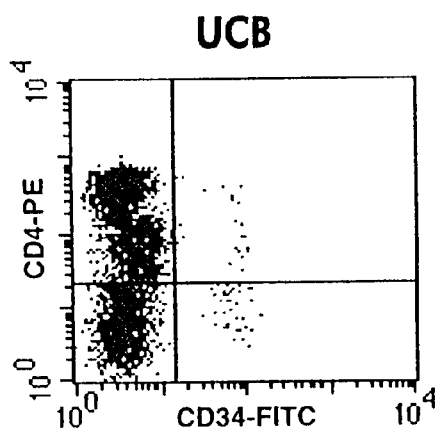
Figure 2J:
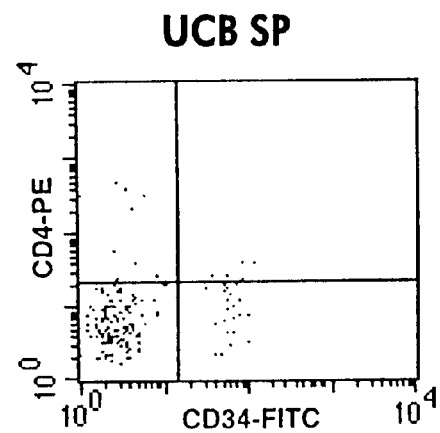

Having defined the UCB SP, the cells that comprise this population were characterized by staining the UCB with Hoechst in conjunction with antibodies directed at specific surface markers. Since a number of in vitro and chimeric animal assays have found that primitive human HSC express high levels of CD34 and low to undetectable levels of CD38 (Hao et al, Blood 86:3745 (1995); Muench et al, Blood 83:3170 (1994); Rusten et al, Blood 84:1473)) the expression of these markers on UCB SP cells was evaluated (FIG. 2). The CD34⁺CD38$^{lo}$/⁻ cells comprised 0.2% (±0.1%) of the total UCB population but comprised 3.8% (±2.7%) of the UCB SP. Thus, the UCB SP was enriched 19-fold for CD34⁺CD38$^{lo}$/⁻ cells; however, only 5–10% of the total cells with this primitive immunophenotype were within the SP. Despite this enrichment for CD34⁺CD38$^{lo}$/⁻ cells, the majority of the UCB SP cells were CD34⁻ (FIG. 2B). All of the CD34⁻SP cells expressed CD45 (FIG. 2D), a pan-leukocyte marker, confirming that these were hematopoietic and not mesenchymal cells.

To more carefully define which cells comprised the CD34⁻SP fraction, UCB was stained with antibodies directed at various lineage commitment markers in combination the Hoechst staining. Cells expressing CD33 or CD19 were not present in the CD34⁻SP (FIG. 2F), indicating an absence of mature myeloid or B-cells. In contrast, a number of CD34⁻SP cells expressed markers commonly found on NK cells (i.e. CD16 and CD56, FIG. 2H). A small fraction of the UCB SP cells also expressed markers associated with mature T-lymphocytes (i.e. CD4, FIG. 2J and CD8). Finally, a more substantial fraction of these cells expressed additional lymphoid markers that might suggest commitment to T-cell differentiation including CD2, CD3, and CD5. These data indicate that, in addition to CD34⁺CD38$^{lo}$/⁻ cells, the UCB SP contained significant numbers of CD34⁻ cells expressing surface markers associated with cells committed to the NK and T-cell lineages.

Example 3

Characterization of SP Cells in Lin⁻UCB

Despite the fact that many of the CD34⁻SP cells in unfractionated UCB appeared to be T-cells and NK cells, a sub-population of CD34⁻SP cells did not stain for T-cell or NK cell markers. To define the nature of this population more clearly, lineage committed cells were depleted from the UCB prior to staining the resulting Lin⁻UCB with Hoechst. The lineage depletion employed high density magnetic separation to specifically deplete cells expressing CD2, CD3, CD14, CD16, CD19, CD24, CD56, CD66b, and glycophorin A (Thomas et al, J. Immunol. Methods 154:245 (1992)). Typically 99.5% of the white cells from umbilical cord blood were removed by this procedure. In 22 sorts where UCB cells were stained with Hoechst 33342, the Lin⁻UCB was enriched 4.7 fold for SP cells relative to the unfractionated UCB (FIGS. 3A–3C). The Lin⁻SP cells remained sensitive to verapamil, similar to the unfractionated UCB SP cells.

Figure 4A:
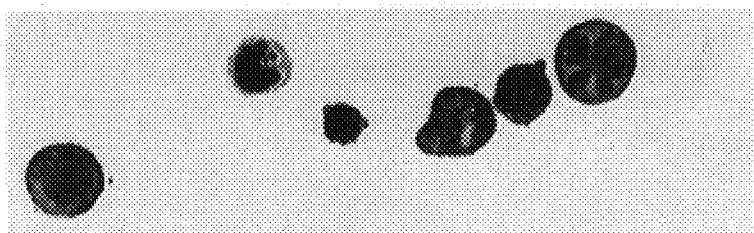
FIGS. 4A–4C. Morphology of purified CD34$^+$ and CD34$^-$Lin$^-$SP cells. Cytopreparations of Lin$^-$UCB (FIG. 4A), CD34$^+$Lin$^-$SP (FIG. 4B) and CD34$^-$Lin$^-$SP (FIG. 4C) cells were stained with Wright-Giemsa stain for comparisons of morphology.
Figure 4B:
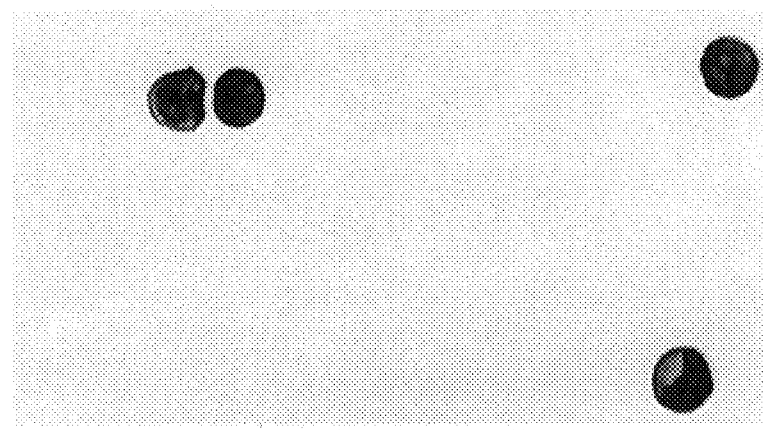
Figure 4C:
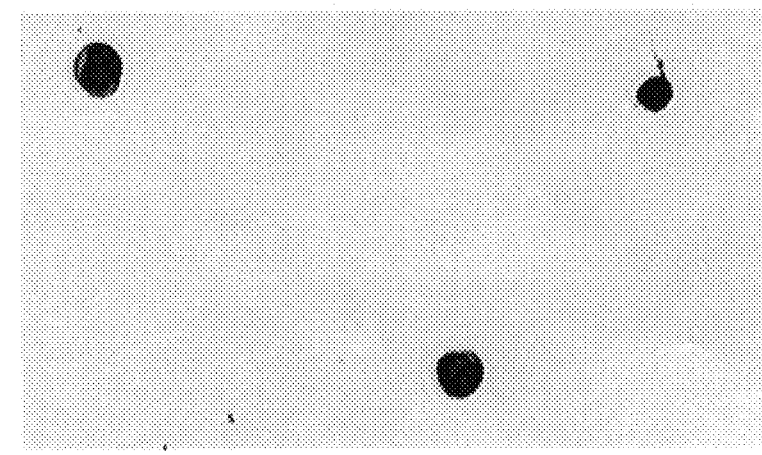

The enrichment for the Lin⁻SP fraction resulted in the purification of a population of cells with low forward and side light scatter properties in FACS® analyses. The Lin⁻SP contained nearly equivalent proportions of 2 distinct subpopulation of cells, one that was CD34⁺(47.5±19.9%) and one that was CD34⁻ (52.5±19.9%;). The CD34⁻ cells within the Lin⁻SP exhibited lower forward light scattering cells than the CD34⁺Lin⁻SP cells. Both subpopulations of cells expressed CD45 (FIGS. 3D–3F), indicating that they were hematopoietic rather than mesenchymal cells. Both the CD34⁺ and CD34⁻Lin⁻SP cells were small blast cells with minimal internal complexity and cytoplasm (FIG. 4), as had been suggested by their light scatter properties. However, the CD34⁻Lin⁻SP cells were distinctly smaller than the CD34⁺ cells.

Figure 5A:
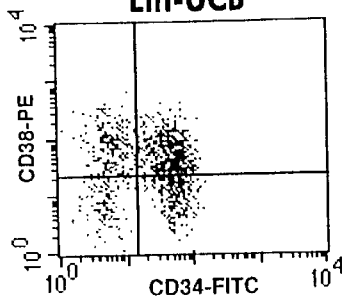
FIGS. 5A–5H. Lack of expression of lineage commitment markers in the Lin$^-$SP. Four-color FACS® analyses were used to compare Lin$^-$UCB (FIGS. 5A, 5C, 5E and 5G) with the Lin$^-$SP (FIGS. 5B, 5D, 5F and 5H). In these analyses, the Lin$^-$SP was defined as the dimmest 0.5% of the Hoechst-stained cells. The expression of CD34 was examined relative to that the expression of CD38 (FIGS. 5A and 5B), CD33 (FIGS. 5C and 5D), CD16 and CD56 (FIGS. 5E and 5F) and CD4 (FIGS. 5G and 5H).
Figure 5B:
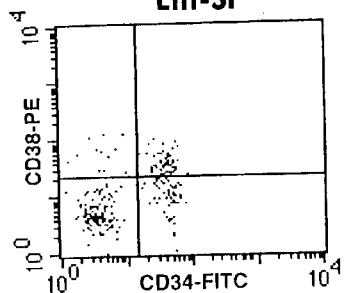
Figure 5C:
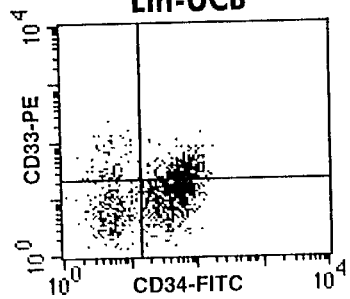

The Lin⁻SP had nearly equivalent proportions of CD34⁺ and CD34⁻ cells, as was observed in the parental Lin⁻UCB population. However, the Lin⁻SP specifically excluded CD34$^{dim}$ cells and exhibited a generalized loss of CD38 positivity when compared with the parental Lin⁻UCB population (FIGS. 5A and 5B). The Lin⁻SP was enriched for both CD34⁺CD38⁻ (16.5±8%) and CD34⁻CD38⁻ (39.7±21.5%) cells when compared with the unmanipulated Lin⁻UCB (8.6±6.3% and 9.5±4.9%, respectively). To ensure that the CD34⁻ cells within the Lin⁻SP did not merely express an alternate isoform of CD34, Lin⁻SP cells were stained with a pool of anti-CD34 antibodies that included three monoclonal reagents (QBEnd10, Immu-133 and Immu-409). Using this reagent, the distinct CD34⁻ and CD34⁺ subpopulations were still observed within the Lin⁻SP.

Example 4

Figure 5D:
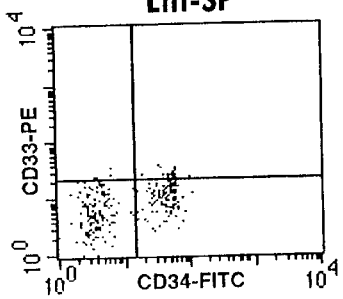
Figure 5E:
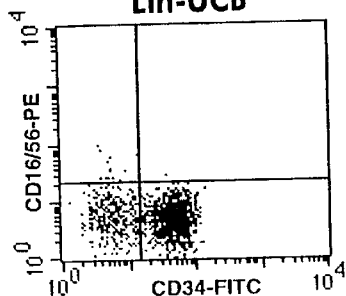
Figure 5F:
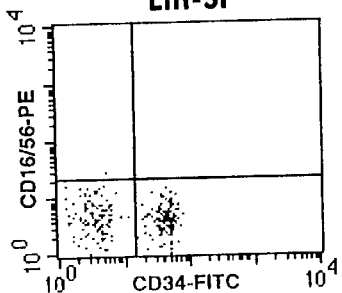
Figure 5G:
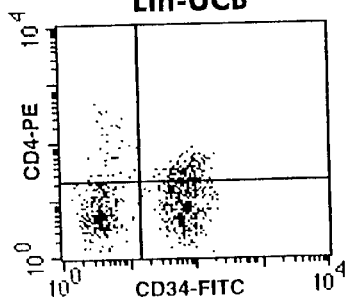
Figure 5H:
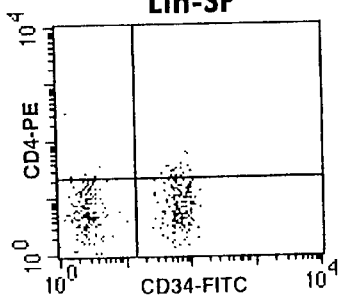
Figure 6A:
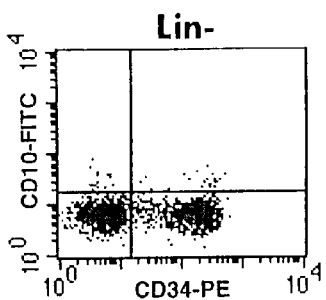
FIGS. 6A–6P. Expression of early lymphoid markers within the Lin$^-$SP. Four-color FACS® analyses were used to compare the expression of CD10 (FIGS. 6A and 6B) and CD7 (FIGS. 6C and 6D) in Lin$^-$UCB (FIGS. 6A and 6C) with that found within the Lin$^-$SP (panels 6B and 6D). These are represented relative to the expression of CD34. The expression of CD3 on the cell surface is (FIGS. 6E and 6F) and in the cytosol (FIGS. 6G and 6H) were compared in Lin$^-$UCB (FIGS. 6E and 6G) and in Lin$^-$SP cells (FIGS. 6F and 6H) that had been isolated by FACS® sorting Hoechst-stained cells. These are represented relative to the surface expression of CD34. Four-color FACS® analyses were used to compare the expression of CD1a (FIGS. 6I and 6J), CD2 (FIGS. 6K and 6L), CD11b (FIGS. 6M and 6N) and CD45RA (FIGS. 6O and 6P) on Lin$^-$UCB (FIGS. 6I, 6K, 6M and 6O) and Lin⁻SP cells (FIGS. 6J, 6L, 6N and 6P). These are represented relative to the expression of CD7. The expression of CD7 is portrayed on the ordinate axis regardless of the fluorochrome used.
Figure 6B:
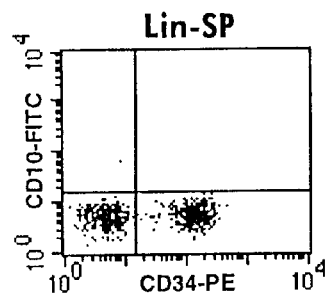
Figure 6C:
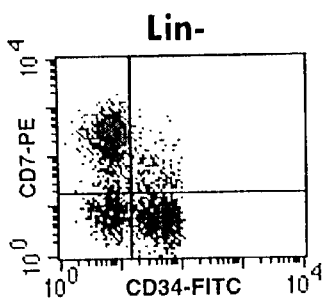
Figure 6D:
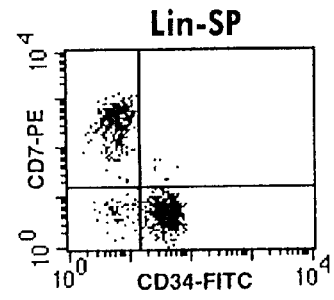
Figure 6E:
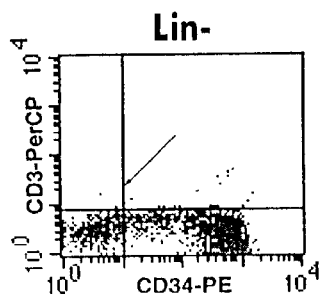
Figure 6F:
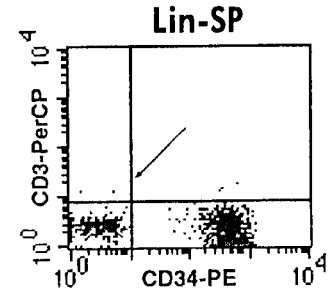
Figure 6G:
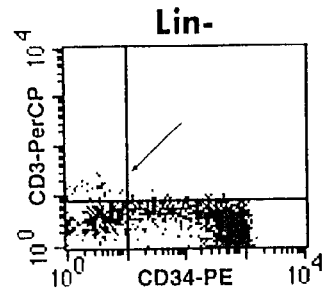
Figure 6H:
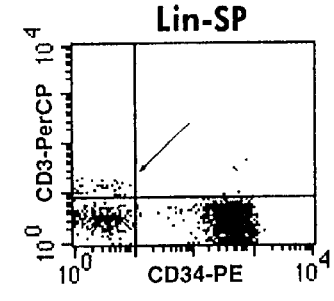
Figure 6I:
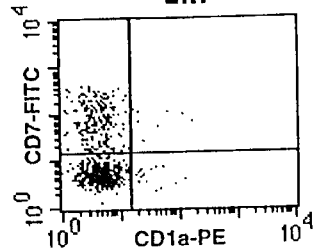
Figure 6J:
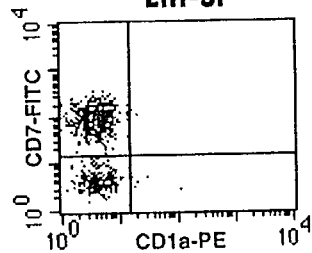
Figure 6K:
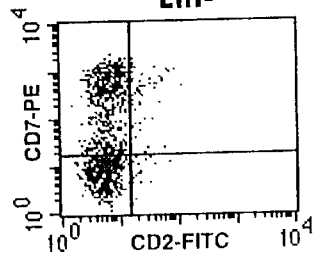
Figure 6L:
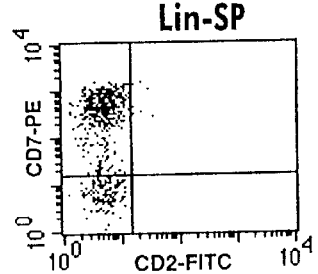
Figure 6M:
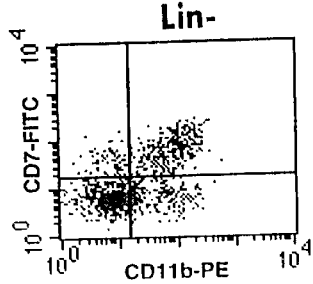
Figure 6N:
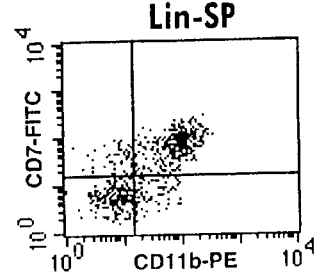
Figure 6O:
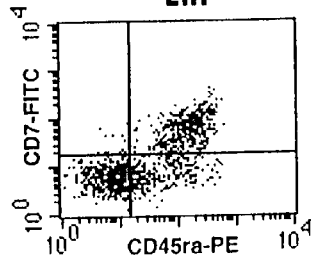
Figure 6P:
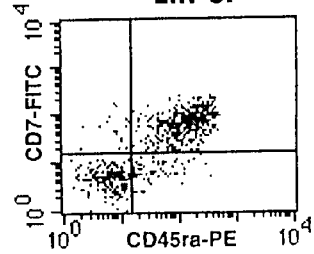

Characterization of Lin⁻CD34⁻SP Cells for the Expression of Lineage Commitment Markers To determine whether lineage committed cells persisted in the Lin⁻SP, these cells were initially evaluated for their expression of cell surface markers commonly found on mature myeloid, lymphoid or NK cells. The Lin⁻SP was largely devoid of CD34⁻CD38⁺ cells. The Lin⁻SP cells did not express significant levels of CD33 (FIG. 5D) or CD19. Thus, as had also been evident in the UCB SP, the Lin⁻SP cells did not contain mature myeloid or B-lymphoid cells. In addition, few of the Lin⁻SP cells expressed CD16 or CD56 (FIG. 5F), CD4 (FIG. 5H) or other surface markers that might be consistent with mature NK or T-cells (eg. CD3 or CD8). Thus, in contrast to the unfractionated UCB SP, significant numbers of cells expressing T-lymphoid and NK surface markers were not present in the Lin⁻SP. To determine whether the Lin⁻SP contained more primitive lymphoid committed cells, the Lin⁻UCB was stained with Hoechst in conjunction with antibodies specific for the early B-cell marker CD10 or the early T-cell marker CD7. The Lin⁻SP cells did not express CD10 (FIG. 6B), indicating these cells were not obviously early B-lymphocytes. Intriguingly, the majority of the CD34⁻Lin⁻SP cells exhibited very bright expression of CD7, whereas the CD34⁺Lin⁻SP cells were devoid of CD7 expression (FIG. 6D). Thus, CD7 and CD34 could be used as markers to discriminate the Line SP populations. Since CD7 is expressed on intrathymic T-cell progenitors (Haynes et al, J. Exp. Med. 168.1061 (1988); KurtzIlerg et al, Proc. Natl. Acad. Sci. USA 86:7575 (1989); Spitz, Curr. Opin. Immunol. 6:213 (1994)) the Lin⁻SP cells were further characterized for the expression of other lineage commitment markers commonly expressed on intrathymic lymphoid progenitors. The Lin⁻SP was entirely negative for surface expression of CD3 (surCD3; FIG. 6F). Approximately 10–30% of the CD34⁻Lin⁻SP cells expressed intracytoplasmic CD3 (cytCD3; FIG. 6H), however, the majority of the CD34⁻Lin⁻SP cells were negative for this marker. The Lin⁻SP cells also did not express CD1a (FIG. 6J), CD2 (FIG. 6L), CD4 (see FIG. 5H), CD5 or CD8. In contrast, virtually all of the CD7⁺ cells co-expressed CD11b (FIG. 6N) and CD45RA (FIG. 6P) as has been described for fetal intrahepatic lymphoid progenitors (Hori et al, Blood 80:1270 (1992)). In summary, the Lin⁻CD34⁻SP cells have an immunophenotype of CD7⁺CD38⁻CD11b⁺CD45RA⁺ and a subset are intracytoplasmic CD3⁺. While some of these markers suggest that these cells have committed to either T-lymphoid or NK cell differentiation, the absence of expression of CD1a, CD2, CD4, surCD3, CD5, CD8, CD16 and CD56 make it impossible to assign these cells to any previously defined stage of T-cell or NK cell development (Spitz, Curr. Opin. Immunol. 6:212 (1994)).

Example 5

Figure 7A:
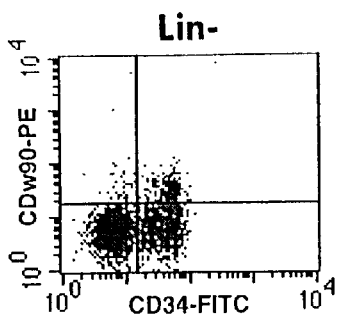
FIGS. 7A–7H. Expression of markers for hematopoietic progenitors in the Lin⁻SP. Four-color FACS® analyses were used to compare the expression of CDw90 (Thy-1.
Figure 7B:
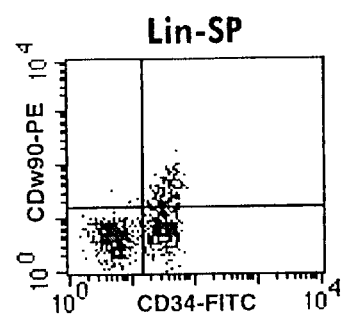
Figure 7C:
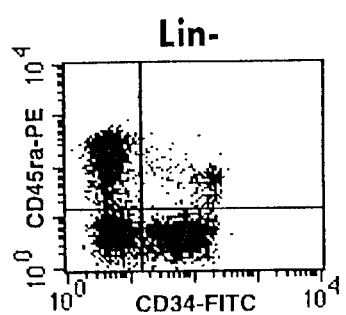
Figure 7D:
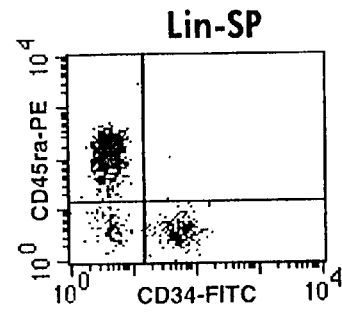
Figure 7E:
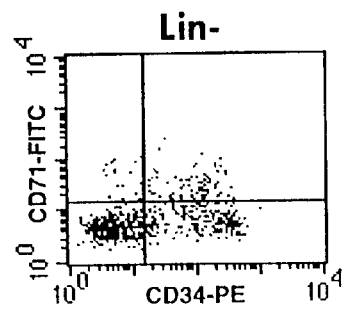

Immunophenotypic Charactenzation of Lin⁻SP Cells for the Presence of Primitive Stem Cell Markers The CD34⁺ cells present in the Lin⁻SP are those cells with the brightest expression of CD34 and which express low to undetectable levels of CD38 (see FIG. 5B). This phenotype had been previously assigned to primitive HSC by a number of groups (Hao et al, Blood 86:3745 (1995); Muench et al, Blood 83:3170 (1994); Rusten et al, Blood 84:1473)). Therefore, the CD34⁺Lin⁻SP cells were evaluated for their expression of other surface markers previously described on primitive human HSC. The CD34⁺Lin⁻SP cells expressed Thy-1 (CDw90) at low to undetectable levels (FIG. 7B). This is similar to the Lin⁻CD34$^{hi}$Thy-1$^{lo}$UCB cell population previously identified by DiGiusto et al that is highly enriched for cells that durably generate multilineage progeny in SCID-hu mice and in long term in vitro cultures (DiGiusto et al, Blood 84:421 (1994)). The CD34⁺Lin⁻SP cells were almost entirely CD45RA⁻ and CD71⁻ (FIGS. 7D and 7F), similar to previously described CD34⁺CD45RA$^{lo}$CD71$^{lo}$ multipotent human stem cells (Terstappen, Blood 77:1218 (1991); Landsorp et al, J. Exp. Md. 178:787 (1993); Thomas et al, J. Immunol. Methods 154:245 (1992)). Furthermore, the CD34⁺Lin⁻SP cells homogenously expressed intermediate levels of HLA-DR (FIG. 7H) consistent with observations that CD34⁺CD38⁻HLA-DR⁺ cells derived from UCB are more enriched for long term culture initiating cells than are the CD34⁺CD38⁻HLA-DR⁻ cells (Cicuttini et al, Growth Factors 10:127 (1994); DeBruyn, Stem Cels 13:281 (1995)). In concert, these observations indicate that the CD34⁺Lin⁻SP cells possess the phenotypic profiles of early hematopoietic progenitor cells as defined by a number of other groups using chimeric animal models and long term in vitro cultures.

Figure 7F:
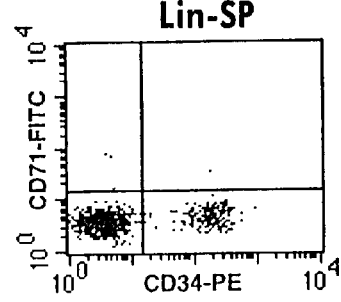
Figure 7G:
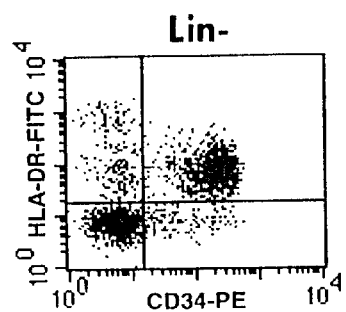
Figure 7H:
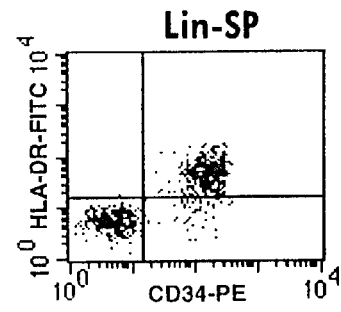

In contrast, the CD7⁺CD34⁻Lin⁻SP cells were CD71⁻ Thy-1⁻ and HLA-DR⁻ (FIGS. 7F, 7B and 7H, respectively). The absence of these surface markers reiterates that these cells are not obviously committed to the erythroid (CD71), T-cell (Thy-1) or B-cell (HLA-DR) lineages.

Example 6

Functional Characterization of Hematopoietic Progenitors in the CD34⁺ and CD34⁻Lin⁻UCB SPs To further determine whether primitive HSC were present in either the CD34⁺ or CD34⁻ fractions of the Lin⁻SP, FACS® isolated cells were plated into hematopoietic progenitor colony assays (HPCA) and long term culture assays (LTCA). Both assays quantify the presence of myeloid and erythroid progenitors. The HPCA is believed to identify relatively mature progenitor cells with limited lineage and self renewal potential, while the LTCA quantifies more primitive cells with a higher self renewal potential. To ensure the highest fidelity possible in isolating cells for establishing HPCA and LTCA, a strategy of multiple sequential sorts was employed. Initially, the SP was sorted as 1–2% of the Hoechst-stained Lin⁻UCB. Since the Lin⁻ cells typically represent only up to 0.5% of the undepleted UCB, this gate corresponded to approximately 0.005–0.01% of the original white blood cell content of the UCB. The sorted Lin⁻SP cells were then restained for sorting on the basis of their expression of CD34 and CD38. The CD34⁺ and CD34⁻ cells were selected, and cells with the brightest CD38 expression were excluded.

The Lin⁻UCB was enriched over 80-fold for HPCA over the starting, unfractionated UCB (FIG. 8A). Following Hoechst-based sorting, the Lin⁻SP population had a lower frequency of clonogenic precursors than did the Lin⁻ cells. This was not unexpected since Lin⁻UCB contains a high proportion of CD38⁺ cells as well as CD34$^{dim}$ cells that can generate colonies in the HPCA and which are eliminated during the isolation of the Lin⁻SP cells. The CD34⁺CD38$^{lo/-}$ Lin⁻SP cells had a clonogenic frequency similar to that of the Lin⁻ cells while the CD34⁻Lin⁻SP cells were essentially devoid of progenitors detectable in the HPCA assay.

Figure 9:
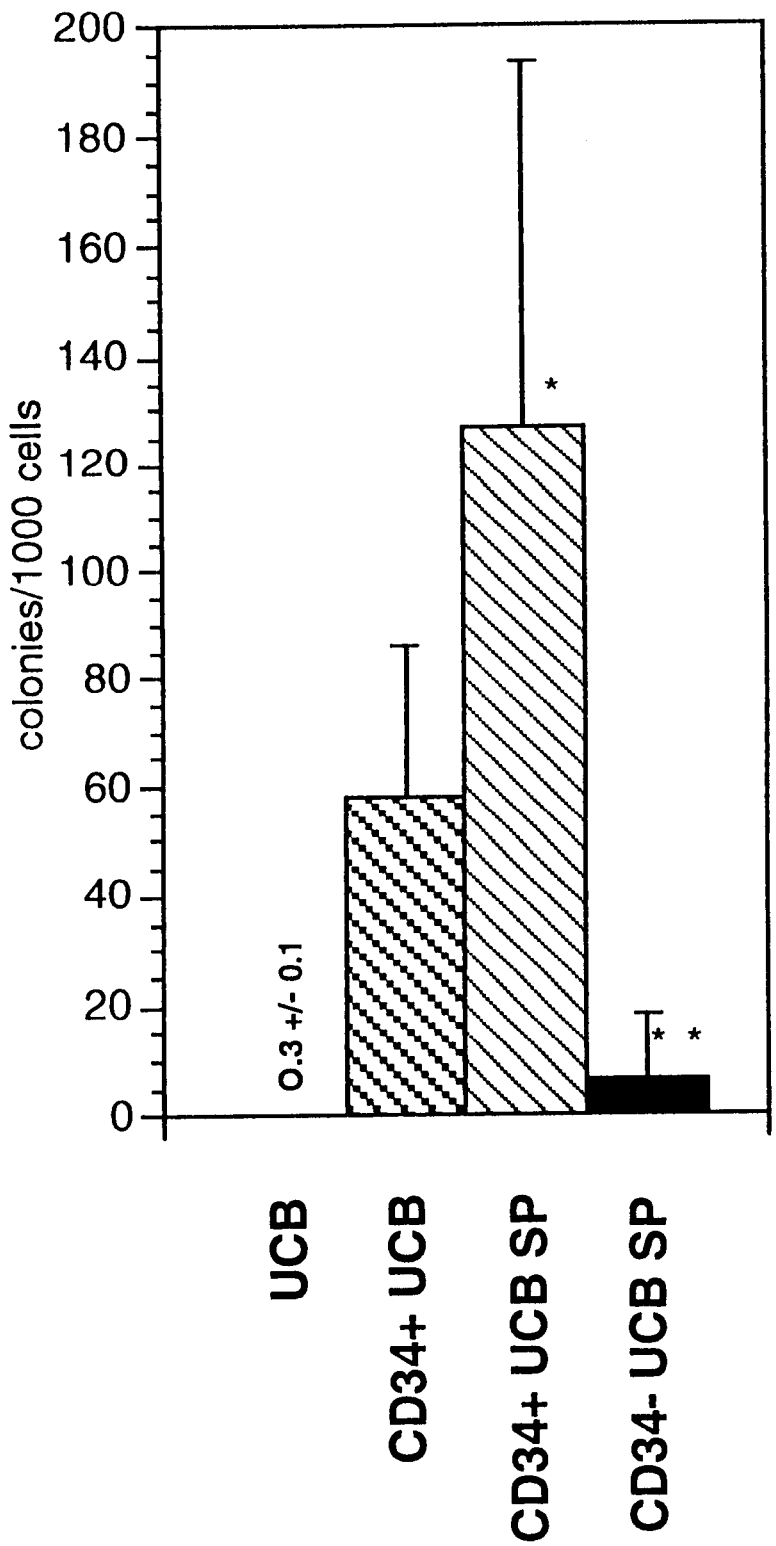
FIG. 9. Growth of UCB SP under myelo-erythroid conditions. UCB SP cells were sorted from unfractionated UCB preparations using 3 color immunocytometry. The hematopoietic progenitors from the sorted cells were enumerated by long term culture on allogeneic bone marrow stroma. The CD34⁺UCB SP cells were excluded from the SP during the sort using a phycoerythrin-conjugated anti-CD34. When feasible, the CD34⁺UCB SP cells were collected separately and cultured. Control cells also included CD34⁺UCB cells that did not lie within the SP gate.

One possible explanation for the failure of CD34⁻ CD38$^{lo/-}$Lin⁻SP cells to grow in the HPCA assay could be that they are too primitive to be supported by the media and cytokines used in the HPCA. To determine whether CD34⁻ Lin⁻SP cells contained more primitive hematopoietic progenitor cells, these cells were placed into long term culture where they were supported on the murine stromal cell line MS-5 for a period of 5 weeks. MS-5 cells support the growth of human multipotent cells and BFU-E for extended periods of time and may support early stem cells as well as, or better than, standard allogeneic stroma (Issaad et al, Blood 81:2916 (1993)). The data from these 5-week long-term cultures reiterate the findings of the HPCA assay (FIG. 8B). Essentially no colonies were derived from the CD7⁺CD34⁻ Lin⁻SP cells while the Lin⁻UCB and the CD34⁺CD38$^{lo/-}$ Lin⁻SP cells were highly enriched for cells capable of generating colonies after 5 week long term cultures. In order to determine whether the lineage depletion procedure or the process of multiple sequential sorts had eliminated CD34⁻ cells capable of generating clonogenic progeny in long term cultures, unfractionated UCB was stained with Hoechst and anti-CD34 and CD34⁺SP and CD34⁻SP cells were recovered and plated onto MS-5 tells for 5-week long term culture assays. Again, essentially no colonies were generated from CD34⁻SP cells while CD34⁺SP were highly enriched for long term culture cells (FIG. 9). In addition, two preliminary experiments, allogeneic bone marrow stroma was also unable to support the growth and differentiation of the CD7⁺CD34⁻Lin⁻SP cells into clonogenic progeny. This indicates that the failure of the CD7⁺CD34⁻Lin⁻SP cells to grow does not result from the use of the MS-5 stroma for supporting long term culture cells.

Example 7

Antibody Combination Specific for Cell Surface Antigens

A combination of antibodies specific for cell surface antigens has been defined that can be used to enrich for a CD7⁺Lin⁻ cell population previously defined using a dye efflux assay. This technology is based on negative selection, where unwanted cells are specifically depleted from sources of stem cells while the cells of interest remain unperturbed.

This cocktail has been used on sources of human umbilical cord blood previously depleted of cells expressing the following cell surface antigens:

| glycophorin A | CD56 | CD66b |
| CD3 | CD24 | CD14 |
| CD2 | CD19 | CD16 |

This initial lineage depletion is achieved using the StemSep kit (StemCell Technologies; Vancouver, BC). The resulting cell preparation is Lin⁻UCB.

To further deplete this Lin⁻UCB population, cells are eliminated that express the following antigens:

| CD38 | CD34 | CD4 |
| CD71 | HLA-DR | CD25 |
| CD33 | CD5 | |

Elimination is effected using flow cytometry.
Cells depleted of these antigens are referred to as Lin⁻Lin⁻ UCB.

To confirm that cells isolated using this depletion enrich for the cells defined based on dye efflux, Lin⁻UCB was prepared using the StemSep kit. These cells were stained with Hoechst 33342 as described above. The cells were then stained with the combination of antibodies directed against additional lineage commitment antigens. The lineage commitment antigens were visualized en masse using a FITC-conjugated secondary antibody directed against mouse immunoglobulin G. The cells were also stained with a PE-conjugated antibody directed against CD7.

Figure 10A:
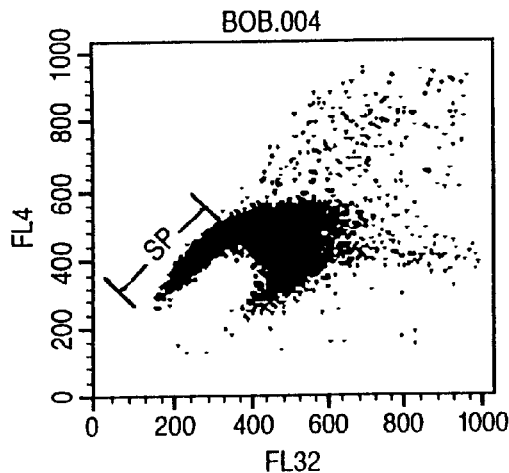
Figure 10B:
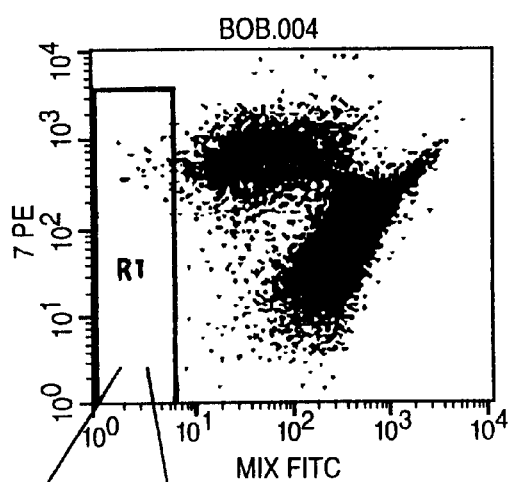
Figure 10C:
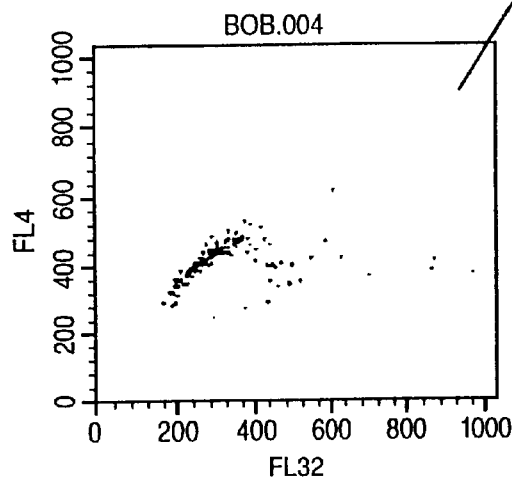
Figure 10D:
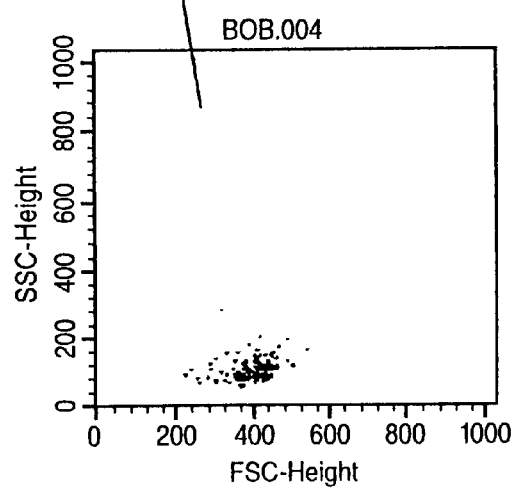

To analyze this complex mixture, data were acquired for 6 cell parameters on a Becton Dickinson FACStar Plus instrument. The Hoechst profile for the total Lin⁻UCB indicated a high Hoechst efflux activity (FIG. 10A). To analyze the Lin⁻Lin⁻UCB, a subpopulation of the total Lin⁻UCB preparation was selected based solely on the lack of expression of the additional lineage commitment antigens (ie FITC negative cells; R1 depicted in FIG. 10B). The cells in this gate were CD7⁺ (FIG. 10B) when analyzed for others parameter the CD7⁺Lin⁻Lin⁻UCB cells were predominantly in the highest efflux portion of the Hoechst profile (FIG. 10C) and were small blast cells (FIG. 10D). These observations were consistent with the cell that had been previously defined using the dye efflux assay.

A similar assay was performed where anti-CD7-PE was replaced with anti-CD59-PE. Some investigators believe that hematopoietic stem cells might express the surface antigen CD59.

Example 8

System that Supports Growth of CD7+CD34−Lin− Cells

Preliminary results indicate that a system has been defined that supports the growth of CD7+CD34−Lin− cells into two distinct cell types. The system involves injecting the cells (derived from human umbilical cord blood) directly into a small piece of human thymus previously transplanted into a SCID (Severe Combined Immune Deficiency) mouse. The thymic grafts were irradiated prior to the transplantation so that all growth in the graft comes from the injected CD7+CD34−Lin− cells. In total, approximately 8000 highly purified CD7+CD34−Lin−SP cells were implanted into the thymic grafts of 4 mice. After 9 weeks, one of the animals that had received the CD7+CD34−Lin−SP cell preparation was sacrificed and the human tissue graft was removed. This thymic graft was populated by immature human T cells that came from the cord blood-derived cells. These preliminary results indicate that the CD7+CD34−Lin−SP cell preparation contains cells capable of becoming T cells. The transplanted cells had expanded greater than 10,000 fold from the initial 2000 cells. Furthermore, the cell dose initially administered was 25 to 100-fold lower than those typically used with purified CD34+ cells in this type of experiment. These preliminary observations indicate that the CD7+CD34−Lin−SP cell preparation is very highly enriched for a progenitor with the potential to repopulate the thymus.

Example 9

Advantages of Including Anti-CD13 Antibodies in the Lineage Depletion Cocktail Antibodies specific for CD4, CD5, CD25, CD33, CD34, CD38, CD71 and HLA-DR can be used, as described in Example 7, to effect purification of CD7+CD34−Lin− cells when applied to Lin− cells previously purified using Stem-Sep stem cell enrichment columns. The degree of purity of these cell preparations ranged frequently from 60% CD7+ to greater than 80% CD7+. The inclusion of antibodies specific for an additional cell surface marker results in a cocktail that can deliver a cell preparation with greater than 80%, if not greater than 90%, purity based on the percentage of CD7+ cells in the final preparation. This marker is CD13 (Becton Dickinson). When Lin−UCB were depleted of cells by the mixture of antibodies set forth above and in Example 7, the resulting population was about 80% pure CD7+ cells. Of those CD7− cells that remained, approximately 15% were CD13+.

This same study indicated that most of the CD7−CD13− cells that remained in the Lin−Lin−UCB cell preparation mark with the cell surface antigen CD41, a platelet marker. Addition of antibodies directed at platelet antigens to the mixture may, however, be disadvantageous since platelets themselves frequently bind cells non-specifically. Therefore, the depletion of platelets may inadvertently deplete cells of interest.

To confirm the identity of CD7+CD34−Lin− cells in the Lin−Lin−UCB after adding anti-CD13 antibodies to the lineage depletion cocktail (resulting in an "extended lineage depletion cocktail"), a Hoechst 33342 dye efflux assay was performed. In this study, the Lin−UCB cells were first labeled with Hoechst 33342 as described above. These cells were then labeled with the extended lineage depletion cocktail using purified antibodies and a secondary FITC conjugated goat anti-(mouse IgG). Finally, the cells were labeled with a PE conjugated anti-CD7 antibody. The Lin−UCB had a typical Hoechst profile. When the CD7+Lin−Lin−UCB cells were gated separately, approximately 50% of the CD7+Lin−Lin−UCB cells localized to the "SP" portion of the profile. This means that the cells purified with the antibody depletion were largely those cells that had originally purified using Hoechst.

To further confirm the identity of CD7+CD34−Lin− cells in the Lin−Lin−UCB after adding anti-CD13 antibodies to the lineage depletion cocktail, immunophenotype of the cells within the Lin−Lin−UCB was performed. The Lin−UCB was labeled with the extended lineage depletion cocktail using an APC conjugated secondary goat anti-(mouse IgG). The cells were subsequently labeled with reagents specific for CD7 and CD11b or for CD7 and CD45RA. The Lin−Lin−UCB cells were predominantly CD7+CD45RA+ and were CD7+CD11b+. These phenotypes confirm that the cells purified with the antibody depletion were largely those cells that had originally been purified using Hoechst.

Example 10

Technique for Monitoring the Activity of the Multidrug Resistance Efflux Pump A technique has been developed whereby the activity of the multidrug resistance efflux pump (MDR) can be monitored within the Lin−Lin−UCB. High MDR activity is a phenotype consistent with hematopoietic stem cells. The activity has been monitored through the efflux of the mitochondrial dye 3,3'-diethyloxacarbacyanine iodide ($DiOC_2$). In these studies, Lin−UCB was first labeled with $DiOC_2$ (50 ng/ml) for 30 minutes, and then washed and allowed to efflux the dye for a period of 90 minutes. The cells were then labeled with the extended lineage depletion cocktail described in Example 9 using an APC conjugated goat anti-(mouse IgG). The cells were then labeled with PE conjugated antibody directed at CD7. The mean value for $DiOC_2$ staining within the CD7+Lin−Lin−UCB was over 100 points lower than for the bulk Lin−UCB population. This indicates that the CD7+Lin−Lin−UCB has a high MDR efflux capacity. This assay has been used to confirm that the original observations with Hoechst 33342 were due to the activity of an MDR efflux pump. This finding is significant in that, since Hoechst is DNA dye, the low Hoechst staining phenotype originally described might be observed in cells with highly condensed chromatin or in cells undergoing apoptosis.

Example 11

CD34−CD7+Lin−/− Cells Proliferiate In Vitro

CD34−CF7+Lin−/− cells have been shown to proliferate on the AFT024 cell line supplemented with various cytokine combinations. More extensive, multi-parameter FACS analysis have been performed to define further the populations that are generated in vitro. FIG. 11 demonstrates that cells with mature NK phenotypes, including CD56+CD16+, CD56+CD16− and CD56−CD16+ cells, were generated from CD34−CF7+Lin−/− cells cultured on AFT024 supplemented with various cytokines. It is expected that cells generated in these cultures possess the functional ability of NK cells to lyse K562 cells. In addition to mature NK cells, other populations with more primitive NK phenotypes, including CD7+CD56+ cells could be readily generated from CD34−CF7+Lin−/− cells. In concert, these observations indicate that the CD34−CF7+Lin−/− cells population contain precursors to NK cells.

In addition to generating cells with NK markers, in certain in vitro culture conditions, the CD34$^-$CD7$^+$Lin$^{-/-}$ cells population generated progeny cells that possess the myeloid CD33 in the absence of other lymphoid markers (see FIG. 12).

Example 12

CD34$^-$CD7$^+$Lin$^{-/-}$ Cells Can Engraft SCID/NOD Mice

Experiments have been conducted that were designed to stringently identify engrafting human cells and to enhance the level of engraftment so that the FACS results are more reliable. In initial experiments, it has been observed that uncultured CD34$^-$CD7$^+$Lin$^{-/-}$ cells are capable of engrafting SCID/NOD mice. In these experiments, only events that stain for the human marker CD45 and fail to stain for the murine marker Ly5.2 are scored as human cells (see FIG. 13). In order to ensure that CD34$^+$ cells did not contribute to engraftment, CD34$^-$CD7$^+$Lin$^{-/-}$ were stringently depleted of any CD34$^+$ cells through multiple purification steps. Using these strict cell isolation and analysis criteria, it has been found that most of the human cells engrafting the SCID/NOD mice are predominantly CD7$^-$, indicating that they are not merely persistent inoculated cells (see FIG. 13). One mouse had sufficient human cells in the spleen to determine that they were predominantly CD19+B-cells (see FIG. 14). A summary of the SCID/NOD repopulating studies performed to date is presented in FIG. 15. Of note, the recipients of unfractionated UCB in these experiments received 10$^7$ cells and the recipients of CD34$^+$Lin$^-$UCB received >500,000 cells. In contrast, the mice inoculated with the recipients of CD34$^-$CD7$^+$Lin$^{-/-}$ cells received ≦4000 cells.

Example 13

CD34$^-$CD7$^+$Lin$^{-/-}$ Cells Can Generate

In addition to the SCID/NOD model of primitive human HSCs, the SCID/hu-thy model has been used to determine whether the CD34$^-$CD7$^+$Lin$^{-/-}$ population contains precursors to T-cells. FIG. 16 demonstrates the engraftment of a series of SCID/hu-thy mice with CD34$^-$CD7$^+$Lin$^{-/-}$ cells. In these experiments, the donor cells are distinguished from any residual host thymocytes by performing transplants of HLA-A2$^+$donor cells into HLA-A2$^-/^-$ recipients. In these experiments, CD34$^-$CD7$^+$Lin$^{-/-}$ cells gave rise to both single positive and double positive HLA-A2$^+$ donor human thymocytes indicating that this population contains T-cell precursors.

Example 14

Negative Depletion

The data shown in FIGS. 17 and 18 demonstrate that it is possible to isolate the stem cell population of the invention with the use of a column based device using either 2 columns sequentially to negatively deplete irrelevant cells (FIG. 17) or a single column to negatively deplete cells (FIG. 18).

All documents cited above are hereby incorporated in their entirety by reference.

One skilled in the art will appreciate from a reading of this disclosure that various changes in form and detail can be made without departing from the true scope of the invention.

What is claimed is:

1. A population of CD34$^-$CD7$^+$Lin$^-$Lin$^-$ hemaotopoietic progenitors comprising greater than about 80% CD7$^+$ cells wherein said CD7$^+$ cells are characterized by a surface phenotype that is CD45RA$^+$, glycophorin A$^-$, CD3$^-$, CD2$^-$, CD56$^-$, CD24$^-$, CD19$^-$, CD66b$^-$, CD14$^-$, CD16$^-$, CD38$^-$, CD71$^-$, CD33$^-$, HLA-DR$^-$, CD5$^-$, CD4$^-$, CD25$^-$ and is capable of multilineage development.

2. The population according to claim 1 wherein said progenitors are isolated from a human cell source selected from the group consisting of umbilical cord blood, bone marrow, peripheral blood and fetal liver.

3. The population of CD34$^-$CD7$^+$Lin$^-$Lin$^-$ hemaotopoietic progenitors according to claim 1 further wherein said progenitors engraft a SCID/NOD mice and develop into CD7$^-$CD45$^+$ lymphoid cells therein.

4. The progenitor population according to claim 3 wherein said cells engraft a SCID/NOD mouse spleen with CD7$^-$CD45$^+$CD19$^+$ human B cells.

5. The population of CD34$^-$CD7$^+$Lin$^-$Lin$^-$ hemaotopoietic progenitor cells according to claim 1 further wherein said progenitors engraft human thymus tissue transplanted into SCID/hu thy mice wherein said progenitors develop into T cell precursors.

6. The progenitor population according to claim 5 further wherein said engrafted T cell precursors develop into lymphocytes expressing CD4$^+$ or CD8$^+$ T cells.

7. A population of CD34$^-$CD7$^+$ hemaotopoietic progenitors comprising greater than about 90% CD7$^+$ cells wherein said CD7$^+$ cells are characterized by a surface phenotype that is CD45RA$^+$, CD13$^-$, glycophorin A$^-$, CD3$^-$, CD2$^-$, CD56$^-$, CD24$^-$, CD19$^-$, CD66b$^-$, CD14$^-$, CD16$^-$, CD38$^-$, CD71$^-$, CD33$^-$, HLA-DR$^-$, CD5$^-$, CD4$^-$, CD25$^-$ and is capable of multilineage development.

8. A population of CD34$^-$CD7$^+$ hemaotopoietic progenitors comprising greater than about 95% CD7$^+$ cells wherein said CD7$^+$ cells are characterized by a surface phenotype that is CD45RA$^+$, CD13$^-$, glycophorin A$^-$, CD3$^-$, CD2$^-$, CD56$^-$, CD24$^-$, CD19$^-$, CD66b$^-$, CD14$^-$, CD16$^-$, CD38$^-$, CD71$^-$, CD33$^-$, HLA-DR$^-$, CD5$^-$, CD4$^-$, CD25$^-$ and is capable of multilineage development.

9. A population of CD34$^-$CD7$^+$ hemaotopoietic progenitors consisting essentially of CD7$^+$ cells wherein said CD7$^+$ cells are further characterized by a surface phenotype that is CD45RA$^+$, glycophorin A$^-$, CD3$^-$, CD2$^-$, CD56$^-$, CD24$^-$, CD19$^-$, CD66b$^-$, CD14$^-$, CD1 6$^-$, CD38$^-$, CD71$^-$, CD33$^-$, HLA-DR$^-$, CD5$^-$, CD4$^-$, CD25$^-$ and is capable of multilineage development.

\* \* \* \* \*

UNITED STATES PATENT AND TRADEMARK OFFICE
CERTIFICATE OF CORRECTION

PATENT NO. : 6,537,807 B1
DATED : March 25, 2003
INVENTOR(S) : Smith et al.

It is certified that error appears in the above-identified patent and that said Letters Patent is hereby corrected as shown below:

Column 3,
Line 17, "wore" should read -- were --;
Line 20, "CD34$^+$" should read -- CD34$^-$ --;
Line 43, "C-CSF" should read -- G-CSF --;
Line 44, "IL11" should read -- IL-11 --; "IL-5" should read -- IL–15 --;
Line 50, "CF7$^{-/-}$" should read -- CF7$^+$ --;
Line 52, "stroina" should read -- stroma --;
Line 60, "Lin$^-$" should read -- Lin $^{-/-}$ --.

Column 4,
Line 12, after "experiments" insert a period (.); "data" should read -- Data --;
Line 15, "5x15" should read -- 5x10$^5$ --.

Column 16,
Line 50, in the sub-heading, "Proliferiate" should read -- Proliferate --;
Line 57, "CD56+CD16+" should read -- CD56$^+$CD16$^+$ --;
Line 58, "CD56+CD16-" should read -- CD56$^+$CD16$^z$ --; "CD56-CD16+" should read -- CD56$^-$ CD16$^+$ --;
Line 64, "CD7+CD56+" should read -- CD7$^+$CD56$^+$ --.

Column 17,
Line 27, "CD19+B-cells" should read -- CD19$^+$B-cells --;
Line 33, ">500,000" should read -- ≥500,000 --;
Line 47, "HLA-A2$^{-/-}$" should read -- HLA-A2$^-$ --.

UNITED STATES PATENT AND TRADEMARK OFFICE
CERTIFICATE OF CORRECTION

PATENT NO. : 6,537,807 B1
DATED : March 25, 2003
INVENTOR(S) : Smith et al.

It is certified that error appears in the above-identified patent and that said Letters Patent is hereby corrected as shown below:

<u>Column 18,</u>
Lines 10, 21-22, 28-29, 36, 43 and 50, "hemaotopoietic" should read
-- Hematopoietic --.

Signed and Sealed this

Sixteenth Day of September, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,537,807 B1
DATED : March 25, 2003
INVENTOR(S) : Smith et al.

It is certified that error appears in the above-identified patent and that said Letters Patent is hereby corrected as shown below:

<u>Column 16,</u>
Line 58, "CD56+CD16-" should read -- $CD56^+CD16^-$ --; "CD56-CD16+" should read -- $CD56^- CD16^+$ --;

Signed and Sealed this

Ninth Day of March, 2004

JON W. DUDAS
*Acting Director of the United States Patent and Trademark Office*